United States Patent
Umeno et al.

(10) Patent No.: US 7,010,990 B2
(45) Date of Patent: Mar. 14, 2006

(54) FORCE DETECTING APPARATUS

(75) Inventors: Takaji Umeno, Nisshin (JP); Katsuhiro Asano, Toyoake (JP); Yoshitoshi Watanabe, Aichi-gun (JP); Masaru Sugai, Aichi-gun (JP); Shu Asami, Nagoya (JP)

(73) Assignee: Kabushiki Kaisha Toyota Chuo Kenkyusho, Aichi-gun (JP)

( * ) Notice: Subject to any disclaimer, the term of this patent is extended or adjusted under 35 U.S.C. 154(b) by 64 days.

(21) Appl. No.: 10/757,465

(22) Filed: Jan. 15, 2004

(65) Prior Publication Data

US 2004/0144173 A1 Jul. 29, 2004

(30) Foreign Application Priority Data

Jan. 16, 2003 (JP) ............................. 2003-008104
Jul. 16, 2003 (JP) ............................. 2003-197740
Oct. 21, 2003 (JP) ............................. 2003-360588

(51) Int. Cl.
*G01L 3/02* (2006.01)

(52) U.S. Cl. ................................. 73/862.326

(58) Field of Classification Search ........... 73/862.331, 73/862.332, 862.333, 862.325, 862.326
See application file for complete search history.

(56) References Cited

U.S. PATENT DOCUMENTS 4,186,597 A * 2/1980 Brown .................. 73/862.328
4,874,053 A * 10/1989 Kimura et al. .............. 180/443
6,456,090 B1 * 9/2002 Ishikawa et al. ............ 324/546
6,550,320 B1 * 4/2003 Giustino ....................... 73/146
2002/0124663 A1 * 9/2002 Tokumoto et al. ...... 73/862.333

FOREIGN PATENT DOCUMENTS

| JP | 4-331336 | 11/1992 |
| JP | 10-506346 | 6/1998 |
| WO | WO 96/10505 | 4/1996 |

* cited by examiner

*Primary Examiner*—Max Noori
(74) *Attorney, Agent, or Firm*—Oblon, Spivak, McClelland, Maier & Neustadt, P.C.

(57) ABSTRACT

In a detecting apparatus, a resolver generates signals whose magnitudes vary periodically in accordance with a positional change of a fixed element side rotating shaft, which is a base for rotation of a rotator and whose position is offset when force of a component parallel to a rotation plane is applied thereto, and in accordance with a rotational state of the tire. An R/D converter generates pulses whose periods correspond to a rotational angle of the rotator and to positional offset of the rotating shaft. From the pulses, a computer detects a characteristic amount which varies in accordance with the positional offset of the shaft. On the basis of the detected amount and a relationship which is determined in advance on the basis of stiffness of the shaft and the amount, the computer detects a moment applied to the shaft, and computes a force generated at the tire.

17 Claims, 33 Drawing Sheets

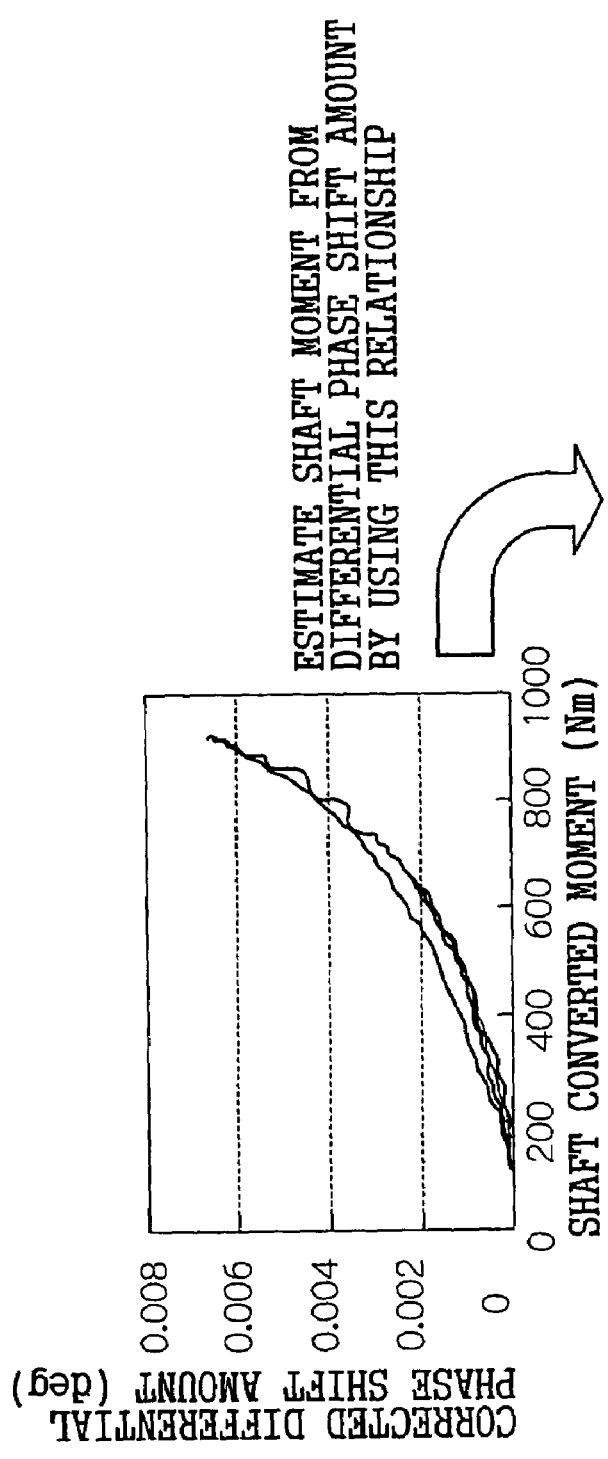
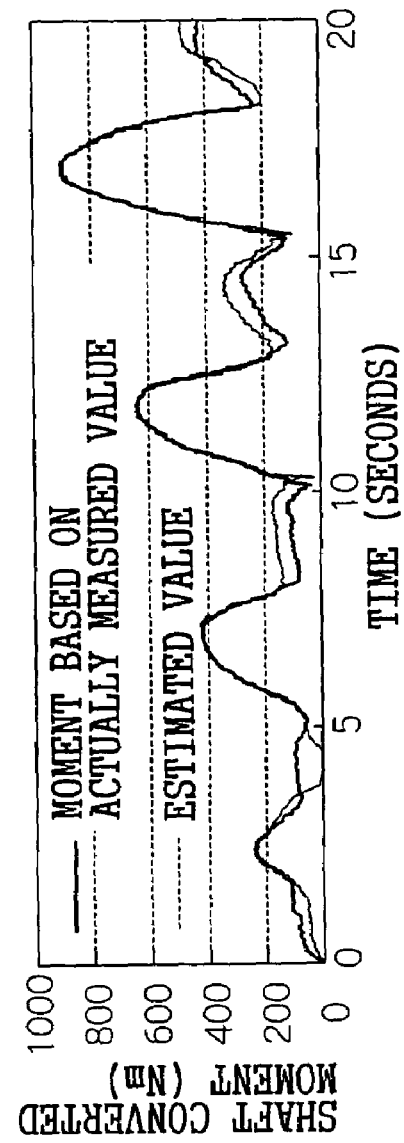
FIG.11A
FIG.11B

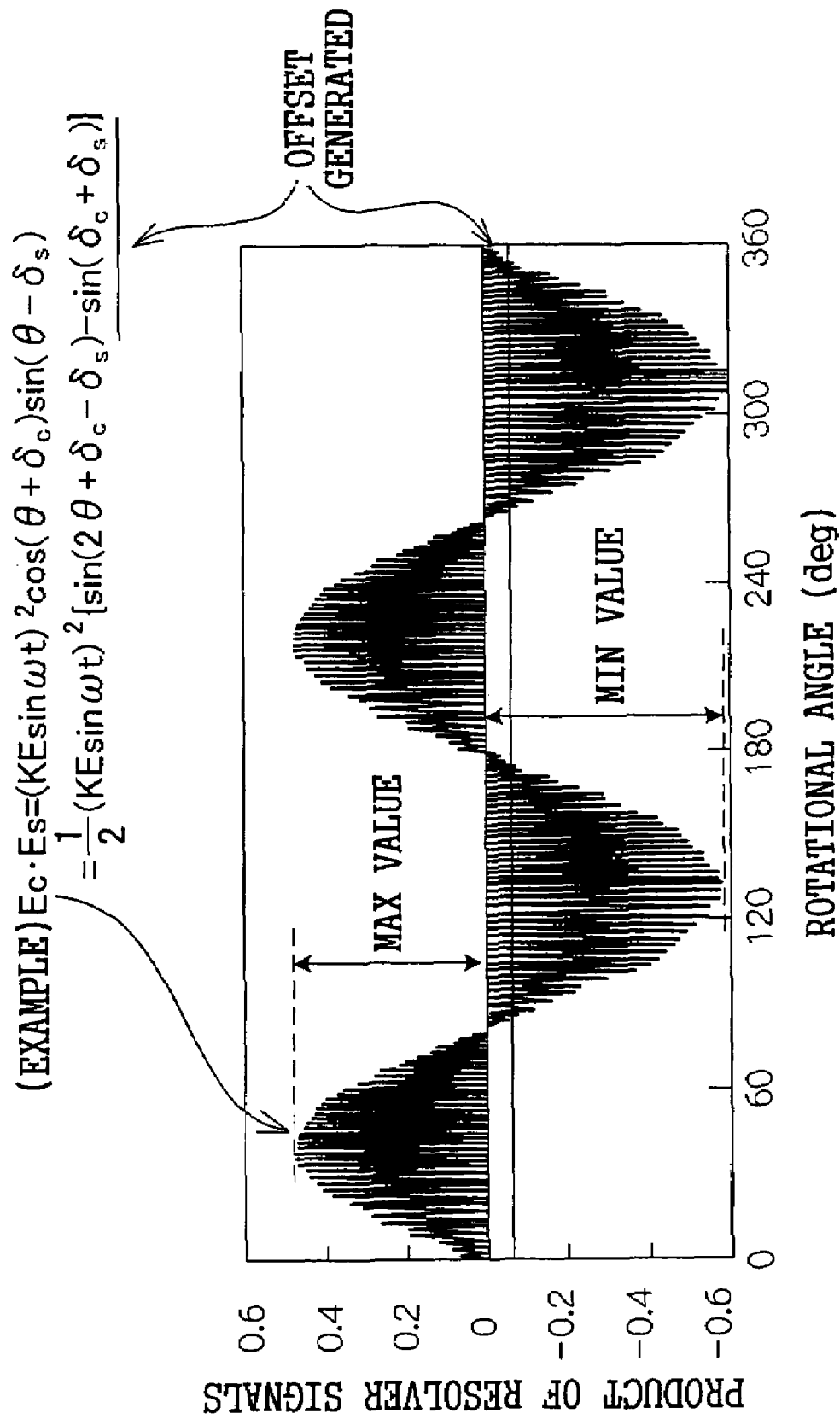

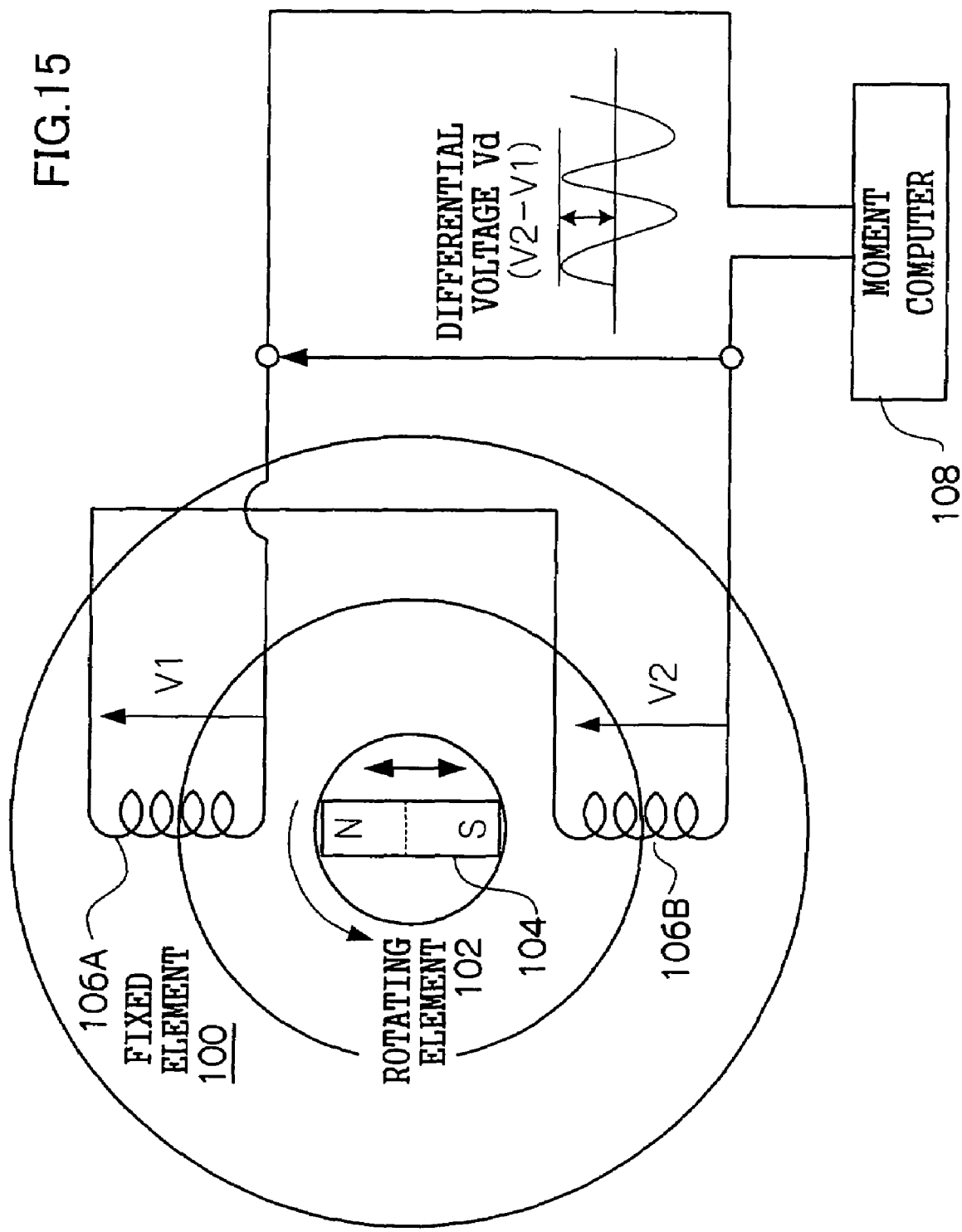

FIG.27A  WHEN ROTATING SHAFT IS AT CENTER
→ PHASE DIFFERENCE BETWEEN V1 AND V2 IS ZERO
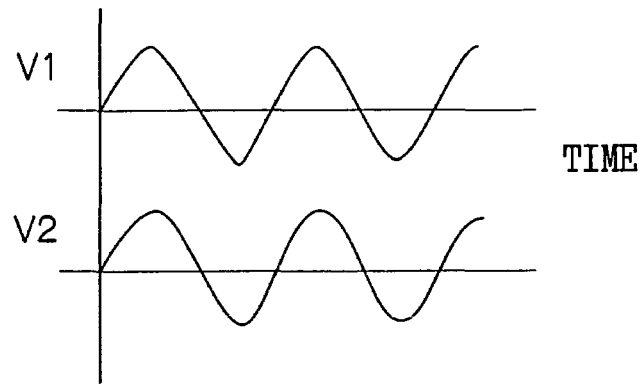
FIG.27B  WHEN ROTATING SHAFT IS DISPLACED
IN THE TOP-BOTTOM DIRECTION
→ A PHASE DIFFERENCE BETWEEN V1 AND V2 ARISES
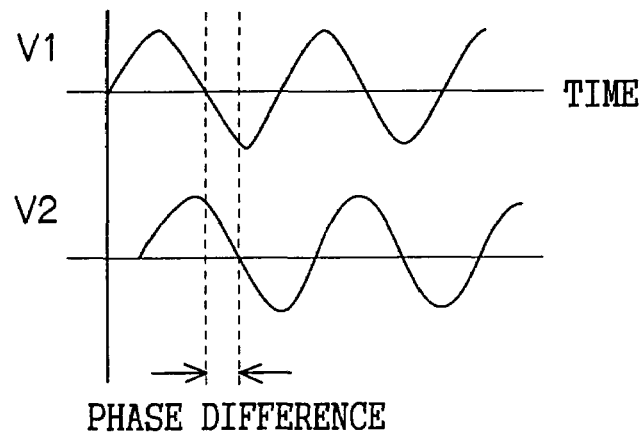
WHEN ROTATING SHAFT IS DISPLACED UPWARD:
THE PHASE OF V2 LAGS

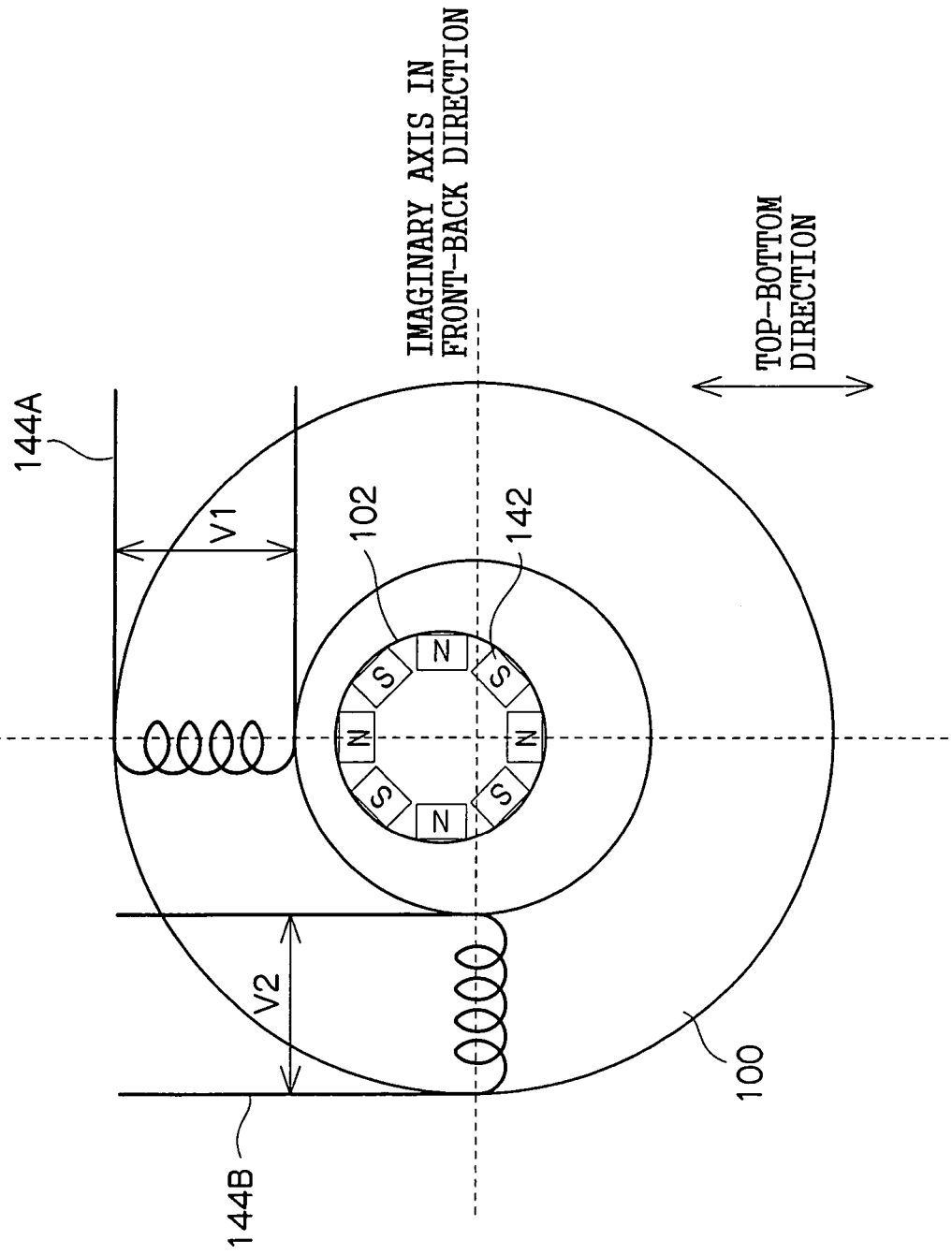

FORCE DETECTING APPARATUS

CROSS-REFERENCE TO RELATED APPLICATION

This application claims priority under 35 USC 119 from Japanese Patent Applications Nos. 2003-360588, 2003-197740 and 2003-008104, the disclosure of which is incorporated by reference herein.

BACKGROUND OF THE INVENTION

1. Technical Field

The present invention relates to a force detecting apparatus. More specifically, the present invention relates to a moment detecting apparatus which detects a moment which is applied to a rotating shaft which is a base for rotation of a rotating body, and to a tire generated force detecting apparatus which detects tire generated forces which are generated between a tire and a road surface.

2. Description of the Related Art

Conventionally, in order to ascertain the frictional state of a tire and to improve the preventive safety control performances of the vehicle (such as preventing lateral slip of a wheel or the like), the tire generated forces which the tire generates, such as the longitudinal force, the self-aligning torque, the lateral force, and the like are sensed.

Japanese Patent Application Laid-Open (JP-A) No. 04-331336 discloses determining the tire generated forces by embedding a strain gauge in the knuckle within the suspension. Japanese Patent Application National Publication No. 10-506346 discloses determining the tire generated forces by embedding a magnetic marker in the surface of the tire and detecting changes in magnetism.

However, in both of the aforementioned techniques, complex machining of the knuckle or the tire must be carried out. These techniques lack wide applicability, the accuracy of detection thereof is poor, and they cannot be considered to be reliable.

SUMMARY OF THE INVENTION

The present invention was developed in consideration of the aforementioned, and an object thereof is to provide a detecting apparatus and a tire generated force detecting apparatus which are reliable.

In order to achieve the above object, a detecting apparatus relating to a first aspect of the present invention comprises: a plurality of signal generating devices each generating a signal whose magnitude varies periodically in accordance with a positional change of a rotating shaft, which is abase for rotation of a rotating body and whose position is offset when force is applied thereto, and in accordance with a rotational state of the rotating body, the signal generating devices being disposed at predetermined positions such that phases of the generated signals are different; a characteristic amount detecting device detecting a characteristic amount corresponding to an amount of positional offset of the rotating shaft, on the basis of the signals generated by the plurality of signal generating devices; and a moment detecting device detecting a moment applied to the rotating shaft on the basis of the characteristic amount detected by the detecting device, and on the basis of a relationship which is determined in advance on the basis of a shaft stiffness of the rotating shaft and the characteristic amount which varies in accordance with the positional offset of the rotating shaft.

The detecting apparatus relating to the present invention has a plurality of signal generating devices which are disposed at predetermined positions such that the phases of the generated signals are different. Each of the plurality of signal generating devices generates a signal whose magnitude varies periodically in accordance with a positional change of a rotating shaft, which is the base for rotation of a rotating body and whose position is offset when force is applied thereto, and in accordance with the rotational state of the rotating body. Specifically, for example, the signal generating device may generate the signal on the basis of the variation in magnetic flux between a fixed element and a rotating element which rotates together with the rotating body. For example, the signal generating device generates the signal on the basis of the electromagnetic induction phenomenon or the Hall effect (seen in semiconductors) or the like which arises between the rotating body and the fixed element. Note that, here, "fixed element" means an object which does not rotate with respect to the rotating body. For example, in a case in which a tire is used as the rotating body, the fixed element is mounted to the vehicle body or the like which does not rotate (i.e., which is fixed).

The characteristic amount detecting device detects a characteristic amount corresponding to the amount of positional offset of the rotating shaft, on the basis of the signals generated by the plurality of signal generating devices.

Here, for example, in a case in which the detecting apparatus has a pulse generating device which generates pulses, whose periods correspond to a rotational angle of the rotating body and the positional offset of the rotating shaft, from the signals generated by the plurality of signal generating devices, the characteristic amount detecting device may detect the characteristic amount from the pulses generated by the pulse generating device.

In this case, the characteristic amount detecting device may comprise a speed change rate computing device determining a speed change rate for each pulse of the rotating body accompanying a positional change of the rotating shaft, from the period of each pulse generated by the pulse generating device during one period of the rotating body, and from an average value of a rotational speed of the rotating body during one period of the rotating body; and a higher-order component computing device detecting, as the characteristic amount, a predetermined higher-order component of the determined speed change rate of the rotating body.

The characteristic amount detecting device may detect, as the characteristic amount, an amount which is dependent on a phase difference of the signals generated by the plurality of signal generating devices.

In this case, the characteristic amount detecting device may detect, as the characteristic amount, an amount of offset of a signal generated by calculating a product of the signals generated by the plurality of signal generating devices.

Further, the characteristic amount detecting device may detect, as the characteristic amount, an amount which is dependent on an amplitude of a signal generated by calculating a difference between the signals generated by the plurality of signal generating devices.

The moment detecting device detects a moment applied to the rotating shaft on the basis of the characteristic amount detected by the detecting device, and a relationship which is determined in advance on the basis of a shaft stiffness of the characteristic amount which varies in accordance with the positional offset of the rotating shaft.

As described above, on the basis of a plurality of signals whose magnitudes vary periodically in accordance with the positional change of a fixed element side rotating shaft, which is the base for rotation of a rotating body and whose position is offset when force of a component parallel to a plane of rotation is applied thereto, and in accordance with the rotational state of the rotating body, the present invention detects a characteristic amount which varies in accordance with the positional offset of the rotating shaft. The present invention detects a moment applied to the rotating shaft on the basis of the detected characteristic amount and on the basis of a relationship which is determined in advance on the basis of the shaft stiffness of the rotating shaft and the characteristic amount which varies in accordance with the positional offset of the rotating shaft. Accordingly, it is possible to provide a moment detecting apparatus which is highly reliable.

The apparatus of the first aspect of the present invention may further have a rotational angle detecting device detecting a rotational angle of the rotating body; and an amplitude detecting device determining amplitudes of the plurality of signals generated by the plurality of signal generating devices. On the basis of the angle detected by the rotational angle detecting device, the characteristic amount detecting device detects, as the characteristic amounts, amplitudes of the plurality of signals determined by the amplitude detecting device when the rotational angle is a predetermined angle.

Namely, the rotational angle detecting device detects the rotational angle of the rotating body. The amplitude detecting device determines the amplitudes of the plurality of signals generated by the plurality of signal generating devices.

Here, the amplitudes of the plural signals, which are determined by the amplitude detecting device when the rotational angle is a predetermined angle, vary in accordance with the amount of positional offset of the rotating shaft.

Thus, on the basis of the angle detected by the rotational angle detecting device, the characteristic amount detecting device of the present invention detects, as the characteristic amounts, the amplitudes of the plurality of signals determined by the amplitude detecting device when the rotational angle is a predetermined angle. Note that the characteristic amount detecting device of the present invention may detect, as the characteristic amount, the amplitude of the product of the plurality of signals determined by the amplitude detecting device when the rotational angle is a predetermined angle.

The moment detecting device detects the moment which is applied to the rotating shaft, on the basis of the detected characteristic amount and a relationship which is determined in advance on the basis of the shaft stiffness of the rotating shaft and the amplitudes of the plurality of signals which are detected as the characteristic amounts varying in accordance with the positional offset of the rotating shaft and which are determined by the amplitude detecting device when the rotational angle is a predetermined angle.

In this way, the amplitudes of the plurality of signals which are determined by the amplitude detecting device when the rotational angle is a predetermined angle, are detected as the characteristic amounts. The amplitudes of the plurality of signals, which vary in accordance with the amount of positional offset of the rotating shaft, are detected at the time when the rotational angle is a predetermined angle. Therefore, even if the rotational speed of the rotating body fluctuates, the characteristic amount can be detected accurately.

Here, the predetermined angle is, for example, an angle which is within a predetermined range which includes a rotational angle which is considered to be a rotational angle of the rotating body at which the amplitudes of the plurality of signals determined by the amplitude detecting device reach the peaks (i.e. become maximums). Note that the predetermined angle may be the rotational angle which is considered to be the rotational angle of the rotating body at which the amplitudes of the plurality of signals become maximums, and may be $(\pi/4)+n \cdot (\pi/2)$, where n is an integer of 0 or more.

The shaft stiffness may be a moment applied to the rotating shaft.

A second aspect of the present invention is a tire generated force detecting apparatus (an apparatus detecting a force generated at a tire) comprising: a plurality of signal generating devices each generating a signal whose magnitude varies periodically in accordance with a positional change of a rotating shaft, which is a base for rotation of a tire mounted to a vehicle and whose position is offset when force is applied thereto, and in accordance with a rotational state of the tire, the signal generating devices being disposed at predetermined positions such that phases of the generated signals are different; a characteristic amount detecting device detecting a characteristic amount corresponding to an amount of positional offset of the rotating shaft, on the basis of the signals generated by the plurality of signal generating devices; and a tire generated force detecting device detecting a tire generated force generated between the tire and a road surface, on the basis of information regarding mechanisms of the tire, and on the basis of the characteristic amount detected by the characteristic amount detecting device, and on the basis of a relationship which is determined in advance on the basis of a shaft stiffness of the rotating shaft and the characteristic amount which varies in accordance with the positional change of the rotating shaft.

In this way, the present invention can detect a tire generated force which is generated between a tire and a road surface, on the basis of information regarding mechanisms of the tire, the detected characteristic amount, and the relationship which is determined in advance on the basis of the shaft stiffness of the rotating shaft and the characteristic amount which varies in accordance with the positional offset of the rotating shaft. Therefore, the present invention can provide a tire generated force detecting apparatus which is reliable.

A third aspect of the present invention is a detecting apparatus comprising: a plurality of signal generating devices each generating a signal whose magnitude varies periodically in accordance with a positional change of a rotating shaft, which is a base for rotation of a tire mounted to a vehicle and whose position is offset when force is applied thereto, and in accordance with a rotational state of the tire, the signal generating devices being disposed at predetermined positions such that phases of the generated signals are different; a rotational angle detecting device detecting a rotational angle of the tire; an amplitude detecting device determining amplitudes of the plurality of signals generated by the plurality of signal generating devices; a detecting device detecting, on the basis of the angle detected by the rotational angle detecting device and the amplitudes of the plurality of signals detected by the amplitude detecting device, a difference between a rotational angle of the tire at which the amplitudes of the plurality of signals become maximums and a rotational angle which is considered to be a rotational angle of the tire at which the amplitudes of the plurality of signals become maximums, and the peaks of the amplitudes of the plurality of signals; and a moment detecting device detecting a moment around an imaginary axis which exists within a plane which is perpendicular to the rotating shaft of the tire, on the basis of the difference in the rotational angles and the peaks which were detected by the detecting device.

In this way, a moment around an imaginary axis which exists within a plane which is perpendicular to the rotating shaft of the tire is detected on the basis of the peaks of the amplitudes of the plurality of signals and on the basis of the difference between a rotational angle of the rotating body at which the amplitudes of the plurality of signals reach the peaks, i.e. become maximums and a rotational angle which is considered to be a rotational angle of the rotating body at which the amplitudes of the plurality of signals reach the peaks, i.e. become maximums. Namely, the rotational angle of the rotating body is used. Therefore, the moment can be detected accurately.

Here, the moment detecting device detects at least one of the moment around an imaginary axis in the horizontal direction of the tire and the moment around an imaginary axis in the vertical direction.

A fourth aspect of the present invention is a detecting apparatus comprising: a pair of signal generating devices each generating a signal whose magnitude varies periodically in accordance with a positional change of a rotating shaft, which is a base for rotation of a tire mounted to a vehicle and whose position is offset when force is applied thereto, and in accordance with a rotational state of the tire, the signal generating devices being disposed at predetermined positions such that phases of the generated signals are different, and being disposed at positions which are offset from one another by a tire rotational angle of 180°, and being disposed at positions which are symmetrical with respect to an imaginary axis in a vertical direction of the tire; a detecting device detecting a difference between the signals generated by the pair of signal generating devices; and a moment detecting device detecting a moment around an imaginary axis which exists within a plane which is perpendicular to the rotating shaft of the tire, on the basis of the difference between the signals generated by the pair of signal generating devices which difference was detected by the detecting device.

In this way, a moment around an imaginary axis which exists within a plane which is perpendicular to the rotating shaft of the tire is detected on the basis of the difference between the signals generated by the pair of signal generating devices. Therefore, the moment around an imaginary axis which exists within a plane which is perpendicular to the rotating shaft of the tire can be divided into a moment around an imaginary axis in the horizontal direction of the tire and a moment around an imaginary axis in the vertical direction, and at least one of these moments can be detected.

Namely, the moment detecting device detects at least one of the moment around an imaginary axis in the horizontal direction of the tire and the moment around an imaginary axis in the vertical direction. Note that the moment around an imaginary axis in the vertical direction of the tire corresponds to the so-called self-aligning torque.

A fifth aspect of the present invention is a detecting apparatus comprising: a pair of signal generating devices each generating a signal whose magnitude varies periodically in accordance with a positional change of a rotating shaft, which is a base for rotation of a tire mounted to a vehicle and whose position is offset when force is applied thereto, and in accordance with a rotational state of the rotating body, the signal generating devices being disposed on an imaginary axis in a tire vertical direction at positions which are offset from one another by a tire rotational angle of 180°; a detecting device detecting a difference between the signals generated by the pair of signal generating devices; and a moment detecting device detecting a moment around an imaginary axis in a horizontal direction of the tire, on the basis of the difference between the signals generated by the pair of signal generating devices which difference was detected by the detecting device.

Namely, in the present invention, it is possible to detect only the moment around an imaginary axis in the horizontal direction of the tire, which is so-called force corresponding to the lateral force.

A sixth aspect of the present invention is a detecting apparatus comprising: a plurality of signal generating devices each generating a signal whose magnitude varies periodically in accordance with a positional change of a rotating shaft, which is a base for rotation of a rotating body attached to a vehicle and whose position is offset when force is applied thereto, and in accordance with a rotational state of the rotating body, the signal generating devices being disposed at predetermined positions such that phases of the generated signals differ when a positional change of the rotating shaft arises; a detecting device detecting a phase difference of the signals generated by the signal generating devices; and a moment detecting device detecting a moment applied to the rotating shaft, on the basis of the phase difference detected by the detecting device.

A seventh aspect of the present invention is a tire generated force detecting apparatus detecting, on the basis of a detected moment, a force generated at a tire, the apparatus comprising: a plurality of signal generating devices each generating a signal whose magnitude varies periodically in accordance with a positional change of a rotating shaft, which is a base for rotation of a tire mounted to a vehicle and whose position is offset when force is applied thereto, and in accordance with a rotational state of the rotating body, the signal generating devices being disposed at predetermined positions such that phases of the generated signals differ when a positional change of the rotating shaft arises; a detecting device detecting a phase difference of the signals generated by the signal generating devices; and a moment detecting device detecting a moment around an imaginary axis which exists within a plane which is perpendicular to the rotating shaft of the tire, on the basis of the phase difference detected by the detecting device.

As described above, because the apparatus of the first and the sixth aspects of the present invention is structured as described above, it has the effect that it can provide a moment detecting apparatus which is very reliable.

Moreover, the present invention detects, as the characteristic amounts, the amplitudes of a plurality of signals which are determined by the amplitude detecting device when the rotational angle is a predetermined angle. The amplitudes of the plural signals, which vary in accordance with the amount of positional offset of the rotating shaft, are detected at a time when the rotational angle is a predetermined angle. Therefore, the present invention has the effect that the characteristic amount can be detected accurately even if the rotational speed of the rotating body fluctuates.

The apparatus of the second aspect of the present invention detects a tire generated force which is generated between a tire and a road surface, on the basis of information relating to mechanisms of the tire, the detected characteristic amount, and a relationship which is determined in advance on the basis of the shaft stiffness of the rotating shaft and the characteristic amount which varies in accordance with the positional offset of the rotating shaft. Therefore, the apparatus of the second aspect has the effect that it is possible to provide a tire generated force detecting apparatus which is very reliable.

The apparatus of the third aspect of the present invention detects the moment around an imaginary axis which exists within a plane which is perpendicular to the rotating shaft of the tire, on the basis of the peaks of the amplitudes of the plurality of signals, and on the basis of the difference between a rotational angle of the rotating body at which the amplitudes of the plurality of signals reach the peaks and a rotational angle which is considered to be a rotational angle of the rotating body at which the amplitudes of the plurality of signals reach the peaks. Namely, the apparatus uses the rotational angle of the rotating body. Therefore, there is the effect that the moment can be detected accurately.

The apparatuses of the fourth aspect and the seventh aspect of the present invention detect a moment around an imaginary axis which exists within a plane which is perpendicular to the rotating shaft of the tire, on the basis of a difference between the signals generated by the pair of signal generating devices. Therefore, these apparatuses have the effect that the moment around an imaginary axis which exists within a plane which is perpendicular to the rotating shaft of the tire can be divided into a moment around an imaginary axis in the horizontal direction of the tire and a moment around an imaginary axis in the vertical direction, and at least one of these moments can be detected.

The apparatus of the fifthe aspect has the effect that it is possible to detect only the moment around an imaginary axis in the horizontal direction of the tire, which is so-called force corresponding to the lateral force.

BRIEF DESCRIPTION OF THE DRAWINGS

FIG. 11A is a diagram showing the relationship between a corrected differential phase shift amount and moment, which are experimental results of the experiment shown in FIG. 10.

FIG. 11B is a graph corresponding to the graph of FIG. 11A and showing results of estimation and actually-measured values of moment.

FIG. 14 is a graph of a signal obtained by multiplying the signals from the resolver.

FIG. 15 is a block diagram of a moment computing apparatus relating to a third embodiment.

FIGS. 27A and 27B are diagrams for explaining the relationship between displacement of a rotating shaft and a phase difference.

FIG. 28 is a diagram showing a state of positional offset of the rotating shaft in the seventh embodiment.

DETAILED DESCRIPTION OF THE INVENTION

Hereinafter, embodiments of the present invention will be described in detail with reference to the drawings.

First Embodiment

Figure 1:
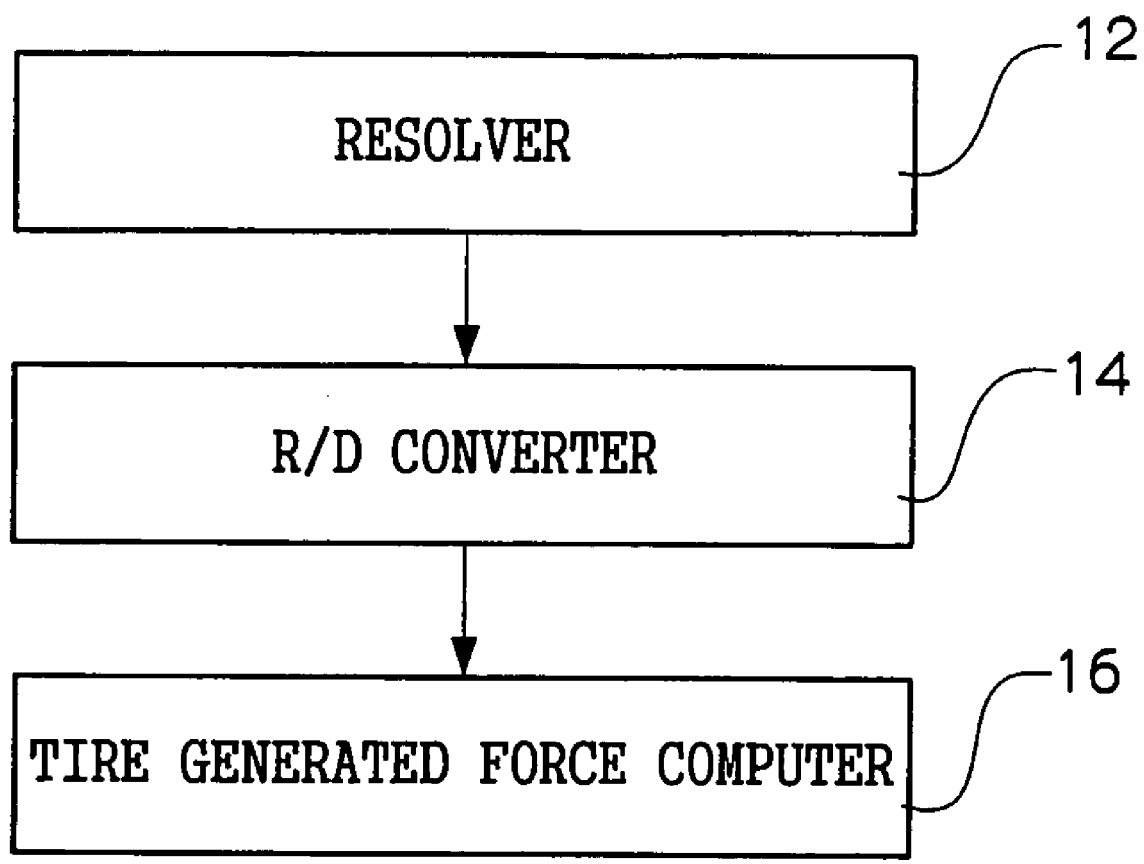
FIG. 1 is a block diagram of a tire generated force computing apparatus relating to a first embodiment.

A first embodiment of the present invention will be described. A tire generated force detecting apparatus (an apparatus detecting forces generated at a tire) relating to the first embodiment is equipped with a moment detecting apparatus of the present invention. As shown in FIG. 1, the tire generated force detecting apparatus relating to the present embodiment has a resolver 12 which is an electromagnetic induction type rotation sensor, a resolver/digital converter (hereinafter called "R/D converter") 14 connected to the resolver 12, and a tire generated force computer 16 connected to the R/D converter 14.

Figure 2:
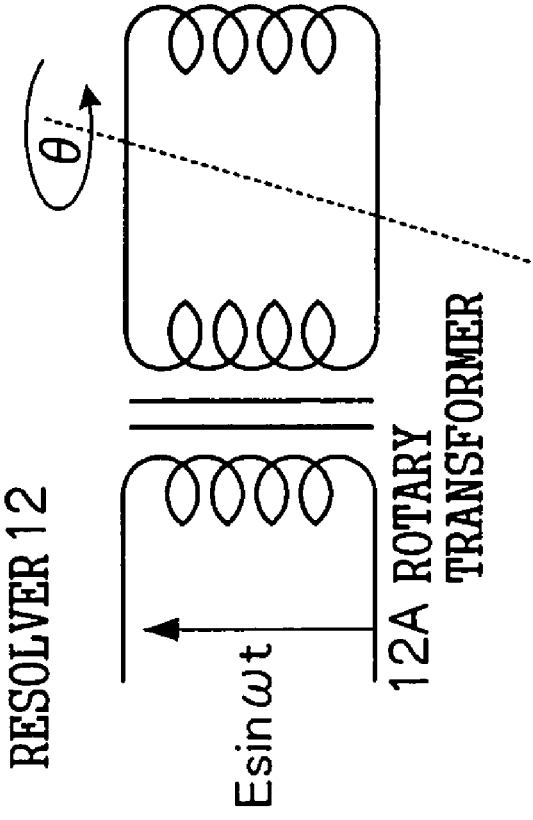
FIG. 2 is a structural diagram of a resolver.

As shown in FIG. 2, the resolver 12 is structured by a rotary transformer 12A, and a plurality of coils 12B at which electromotive force is generated by electromagnetic induction with the output side coil of the rotary transformer 12A. In the present embodiment, two coils 12B1, 12B2 having the same structure are provided. The rotary transformer 12A is mounted to a tire, which is a rotating body, so as to rotate together with the tire. The coils 12B1, 12B2 are wound around a fixed element (not illustrated) which is fixed to the vehicle body.

The coils 12B1, 12B2 generate inducted voltages Ec, Es, respectively, and signals Ec, Es are outputted from the resolver 12. The coils 12B1, 12B2 are disposed at predetermined positions such that the phase difference of the outputted signals Ec, Es is a predetermined value (e.g., 90°). Note that the coils 12B1, 12B2 correspond to the signal generating devices of the present invention, and generate signals whose magnitudes vary periodically in accordance with the rotational state of the tire and changes in the position of an axle at which positional offset arises when lateral force or the like is applied thereto. Detailed operation of the signal generating devices will be described later.

Figure 3:
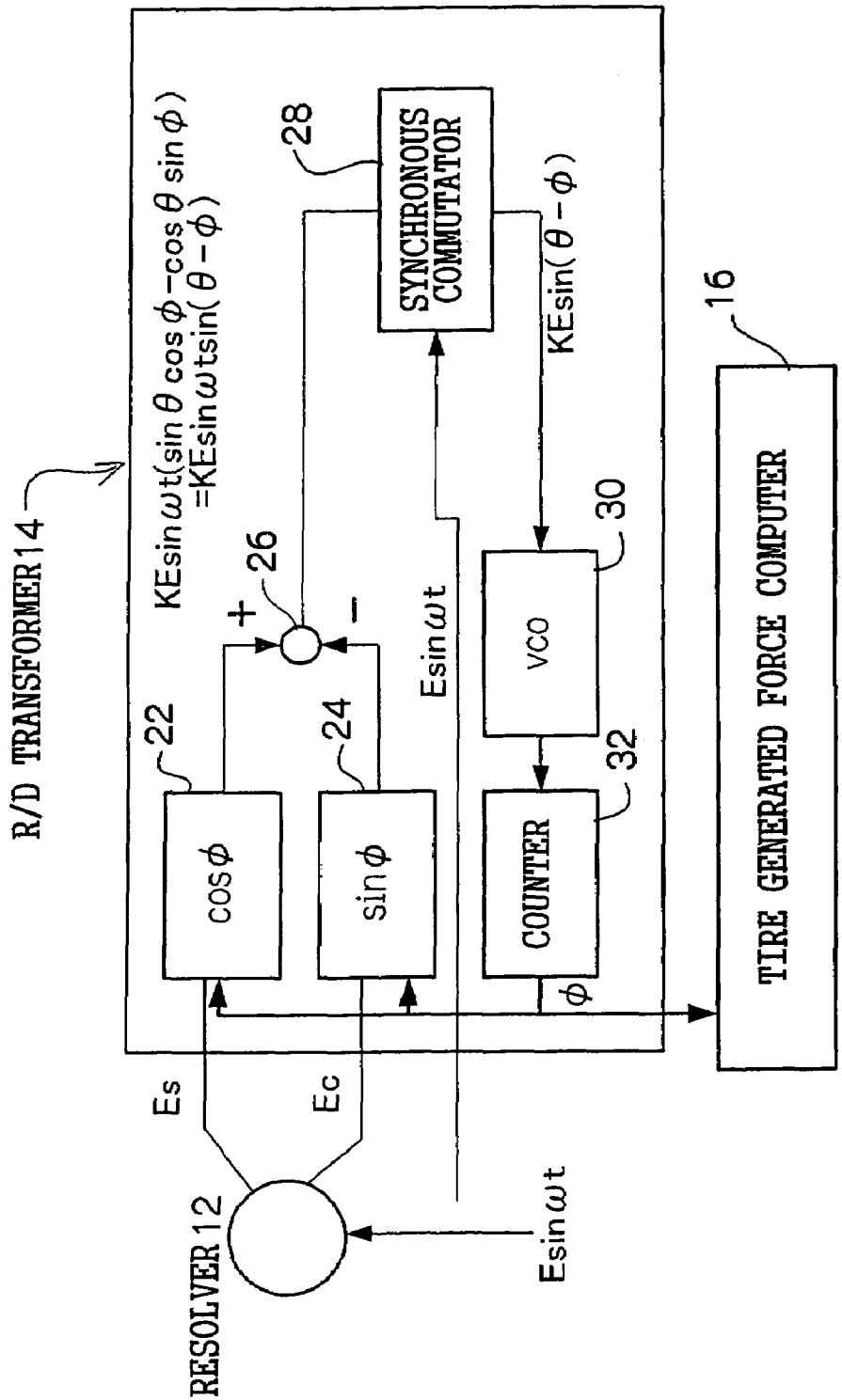
FIG. 3 is a block diagram showing mainly an R/D converter.

As shown in FIG. 3, from the output signals Ec, Es of the resolver 12, the R/D converter 14 generates a pulse whose period corresponds to the rotational angle of the tire and the positional offset of the axle. Note that the R/D converter 14 corresponds to the pulse generating device. More specifically, the R/D converter 14 has a multiplier 22 to which the one signal Es of the signals Ec, Es from the resolver 12 is inputted and which multiplies cos φ by the signal Es, and a multiplier 24 to which the other signal Ec is inputted and which multiplies sin φ by the signal Ec. A subtracter 26, which subtracts the output of the multiplier 24 from the output of the multiplier 22, is connected to the multiplier 22 and the multiplier 24. A synchronous commutator 28 is connected to the subtracter 26. A voltage control oscillator (hereinafter called VCO) 30, which outputs an up-down pulse proportional to the error output, is connected to the synchronous commutator 28. A counter 32, which outputs a digital output angle φ corresponding to the number of inputted pulses, is connected to the VCO 30. The output end of the counter 32 is connected to the multiplier 22, the multiplier 24, and the tire generated force computer 16, respectively.

The tire generated force computer 16 is structured by an unillustrated IC element or the like. On the basis of the output of the counter 32, the tire generated force computer 16 detects a characteristic amount which corresponds to the amount of positional offset of the axle. The tire generated force computer 16 works to detect the moment applied to the axle on the basis of the detected characteristic amount and a relationship which is determined in advance on the basis of the shaft stiffness of the axle and the characteristic amount which varies in accordance with the positional offset of the axle. For example, in the present embodiment, a moment is used as the shaft stiffness of the axle.

Next, the principles of detecting a tire generated force in the present embodiment will be described.

Figure 4:
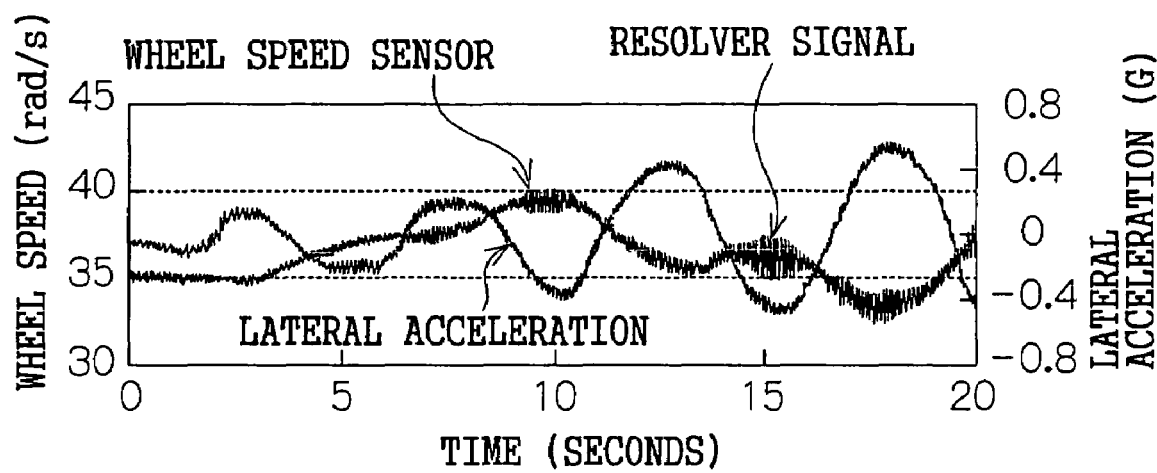
FIG. 4 is a graph showing the relationship between lateral acceleration, wheel speed, and a resolver signal when a vehicle is slaloming.

When the vehicle is slaloming, the lateral force applied to the tire is applied to the axle, and the lateral acceleration gradually increases. As shown in FIG. 4, even if lateral acceleration arises, the wheel speed detected by the wheel speed sensor does not vary that much. In contrast, as the absolute value of the lateral acceleration becomes large (or in other words, as the lateral force becomes large), disturbance arises in the amplitudes of the output signals of the resolver which were described above. Namely, the amplitudes of the output signals of the resolver vary in accordance with the magnitude of the lateral force.

Namely, when lateral force is applied to the tire, a moment arises, and positional offset of the axle, which is the rotating shaft of the tire, thereby arises. In a case in which no positional offset of the axle arises, the gaps (distances) between the output side coil of the rotary transformer 12A mounted to the tire and the coils 12B1, 12B2 mounted to the vehicle body do not change. However, when positional offset of the axle arises, the gaps between the output side coil of the rotary transformer 12A and the coils 12B1, 12B2 vary. In this way, the respective magnetic resistances vary, and changes arise in the induced voltages generated at the coils 12B1, 12B2, respectively.

The relationship between the moment and the characteristic amount which varies in accordance with the positional offset of the axle is measured in advance by a predetermined measuring device or the like, and is stored in advance in a memory or the like of the tire generated force computer 16 by a map, a data table, a relational expression, or the like. The moment can be determined from the relationship stored in advance and the obtained characteristic amount. The tire generated forces which are generated at the tire, such as the longitudinal force, the self-aligning torque, the lateral force, and the like, can be determined from the obtained moment.

Next, operation of the present embodiment will be described.

First, the principles of operation of the R/D converter will be described. As shown in FIG. 2, when a high frequency AC voltage $E \sin \omega t$ (e.g., $\omega = 2\pi f$, f=20 kHz or the like) is applied to the rotary transformer 12A of the resolver 12, voltages expressed by the following equations are induced at the coils 12B2, 12B1 by electromagnetic induction.

$$Ec = KE \cos \theta \sin \omega t$$

$$Es = KE \sin \theta \sin \omega t \qquad \text{Formula 1}$$

Here, K is a coupling coefficient. As can be understood from the above equations, the magnitudes of the induced voltages vary in accordance with a rotational angle θ of the tire.

As shown in FIG. 3, one signal Es of the output signals Ec, Es of the resolver 12 is inputted to the multiplier 22, and cos φ is multiplied by the signal Es. The other signal Ec is inputted to the multiplier 24, and sin φ is multiplied by the signal Ec. The outputs of the multiplier 22 and the multiplier 24 are respectively inputted to the subtracter 26. Because the subtracter 26 subtracts the output of the multiplier 24 from the output of the multiplier 22, the outputted voltage is:

$$KE\sin\omega t(\sin\theta\cos\phi - \cos\theta\sin\phi) = KE\sin\omega t(\sin(\theta-\phi)) \quad \text{Formula 2}$$

A signal $E\sin\omega t$ is inputted to the synchronous commutator 28 from the resolver 12, and the voltage (signal) expressed by the above formula is inputted to the synchronous commutator 28 from the subtracter 26. The synchronous commutator 28 removes the $\sin\omega t$ portion from the signal inputted from the subtracter 26, and outputs the obtained signal $KE\sin(\theta-\phi)$ to the VCO 30.

The VCO 30 outputs to the counter 32 up-down pulses of a number corresponding to the magnitude of the voltage $\sin(\theta-\phi)$ ($\approx\theta-\phi$) which is the error output. Until the output of pulses from the VCO 30 stops, the counter 32 repeatedly inputs the digital output angle $\phi$ corresponding to the number of up-down pulses to the multiplier 22 and the multiplier 24, and adjusts the value of $\phi$ such that the digital output angle $\phi$ coincides with the rotational angle $\theta$. In this way, $\sin(\theta-\phi)=0$. Namely, $\theta=\phi$. The digital output angle $\phi$ becomes equal to the actual rotational angle $\theta$ of the tire.

Figure 5:
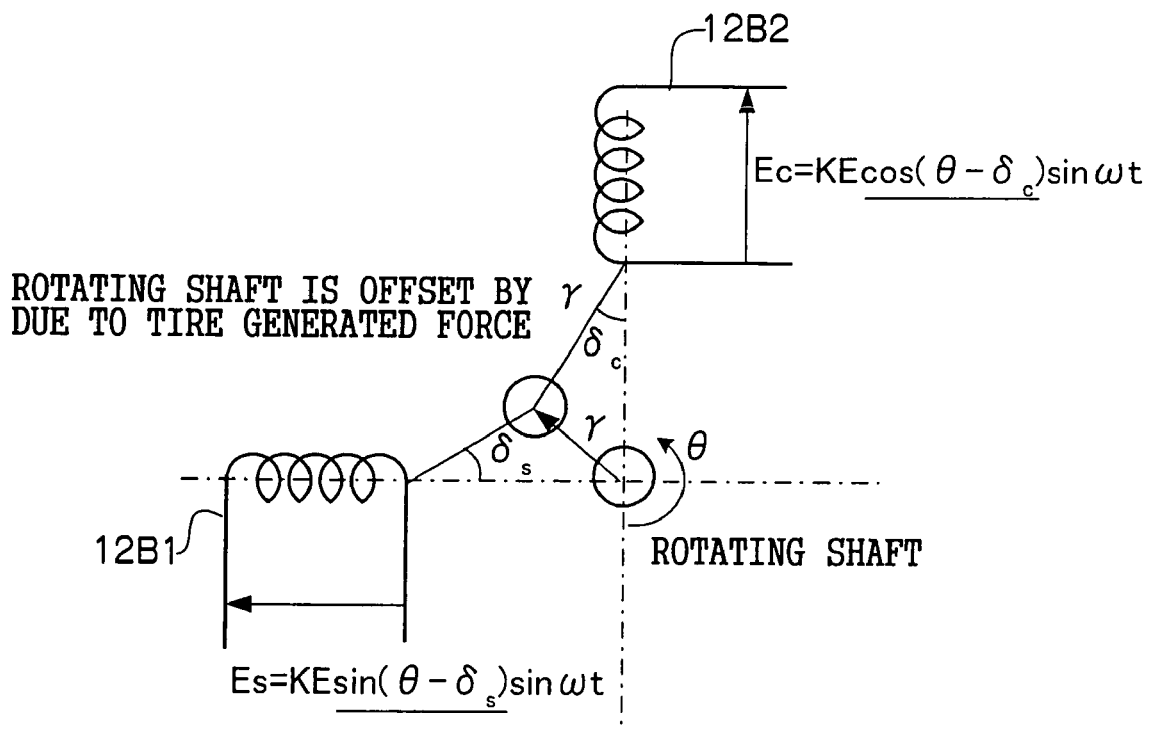
FIG. 5 is a diagram showing induced voltages which have been induced at respective coils at a time when a rotating shaft is offset.

The above describes the principles of operation in a case in which no positional offset of the axle arises. In contrast, as shown in FIG. 5, in a case in which lateral force (a tire generated force) is applied and the position of the axle (the rotating shaft) is offset by $\gamma$, operations are as follows. When offset of the phases of $\delta s$, $\delta c$ arises in the induced voltages of the coils 12B1, 12B2 due to the positional offset of the axle, the induced voltages Ec, Es are as follows:

$$Ec = KE\cos(\theta+\delta_c)\sin\omega t$$

$$Es = KE\sin(\theta-\delta_s)\sin\omega t \quad \text{Formula 3}$$

The induced voltage Ec is inputted to the multiplier 24, and the induced voltage Es is inputted to the multiplier 22. Via the subtracter 26 and the synchronous commutator 28, the VCO 30 and the counter 32 determine the digital output angle $\phi$ such that:

$$\sin(\theta-\delta_s)\cos\phi - \cos(\theta+\delta_c)\sin\phi \to 0 \quad \text{Formula 4}$$

As a result, a pulse, which is the following value which solves the above formula and whose period corresponds to the rotational angle $\theta$ of the tire and the positional offset of the axle, is inputted from the counter 32 to the tire generated force computer 16.

$$\phi = \theta + \frac{1}{2}\{(\delta_c - \delta_s) - (\delta_c + \delta_s)\cos 2\theta\} \quad \text{Formula 5}$$

Figure 6:
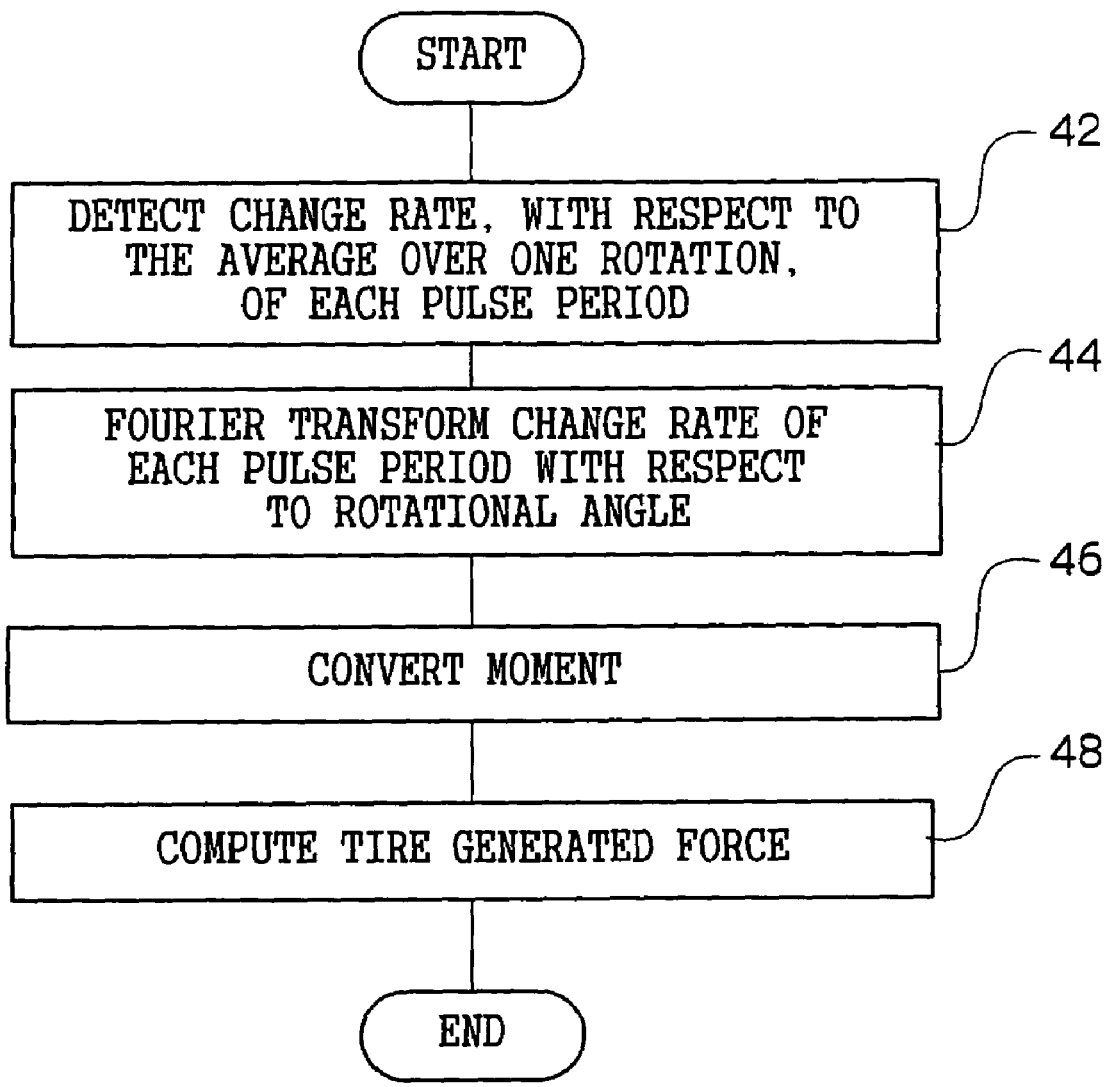
FIG. 6 is a flowchart showing a control routine which a tire generated force computer executes.

The tire generated force computer 16 executes the control routine shown by the flowchart in FIG. 6. Namely, in step 42, a speed change rate, with respect to the average over one rotation, of each pulse period from the R/D converter 14 is detected. Note that this step corresponds to the speed change rate computing device.

First, the instantaneous velocity V hat, which is inputted from the R/D converter 14, is determined. In this way, $$\hat{V} = V + V(\delta_c + \delta_s)\sin 2\theta \quad \text{Formula 6}$$

is determined. By computing the left side of the following formula from V hat ($=d\phi/dt$) and the average value V ($=d\theta/dt$) of the tire rotational speed, the speed change rate is determined. Note that, in a case in which the position of the axle is offset, the speed fluctuates periodically in accordance with this speed change rate.

$$\frac{\hat{V} - V}{V} = (\delta_c + \delta_s)\sin 2\theta \quad \text{Formula 7}$$

Figure 12:
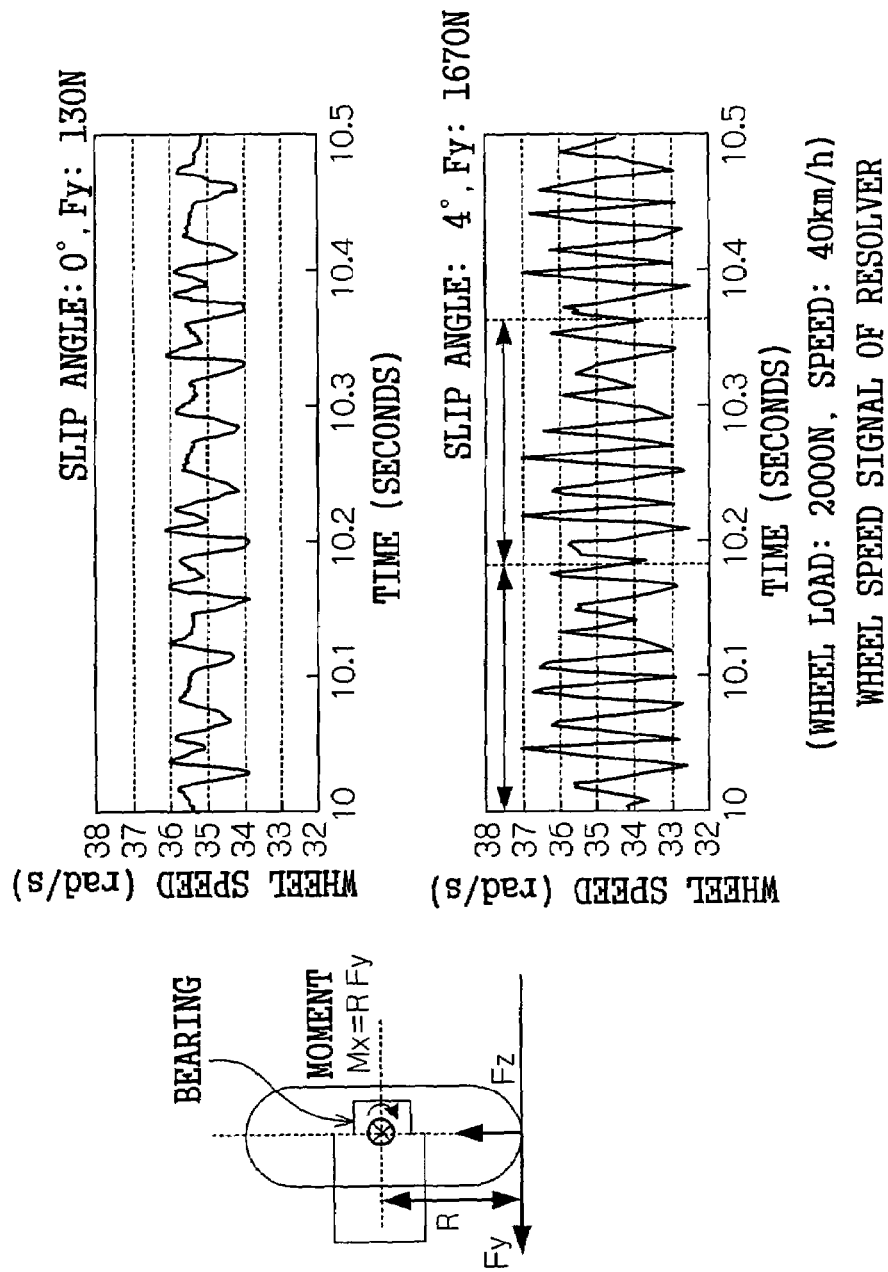
FIG. 12 is a graph showing wheel speed when a slip angle, in a case in which the number of pairs of magnetic magnetic poles is 4, is 0° and 4°.

As can be understood from the above formula, at a half of a rotation of the tire, there is one period, i.e., a frequency of twice the number of rotations of the tire. This is a case in which the number of magnetic magnetic poles (number of coils) of the resolver 12 is two. Generally, given that the number of magnetic magnetic poles is P, the period of the speed change rate (the frequency of the speed change) is P times the number of rotations of the tire. For example, FIG. 12 shows the results of measurement of wheel speed in a case in which the number of magnetic poles is 8. Note that FIG. 12 illustrates the results of measurement of wheel speed for a case in which the rolling direction of the tire is not offset from the direction of traveling of the vehicle (slip angle 0°) and a case in which the vehicle is turned and lateral force is generated (slip angle 4°). As shown in FIG. 12, on the basis of the signals from the resolver 12, a signal of 8 periods is outputted during one rotation of the tire.

As can be understood from the above formula, the differential phase shift amount is unrelated to the rotational speed of the tire.

The change rate of the rotational speed of the tire is determined for each pulse period over one rotation of the tire.

Figure 16A:
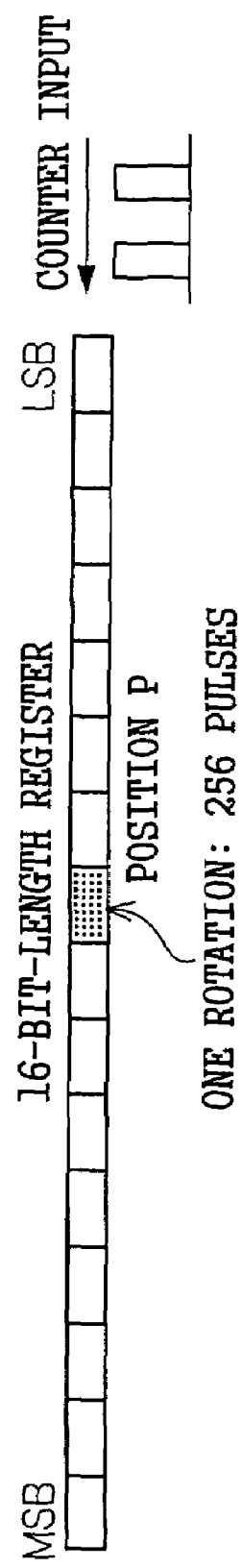
FIGS. 16A and 16B are explanatory diagrams explaining the principles of determining a rotational speed of a tire from the signal of the resolver.

Here, the specifics of determining the speed change rate will be described. When the R/D converter 14 is designed so as to have an angular resolution of 16 bits at one rotation of the resolver by using a 16-bit-length register as the counter, as shown in FIG. 16A, looking at the time-series signal of the MSB of the register, in one rotation, a signal of one pulse rises, and at the LSB, in one rotation, $2^{15}$ (32, 768) pulses rise. Namely, the number of pulses which rise during one rotation differs depending on the bit of the register. For example, at the bit at position P which is 7 positions higher than the LSB in FIG. 16A, a signal of 256 ($=2^8$) appears.

Figure 16B:
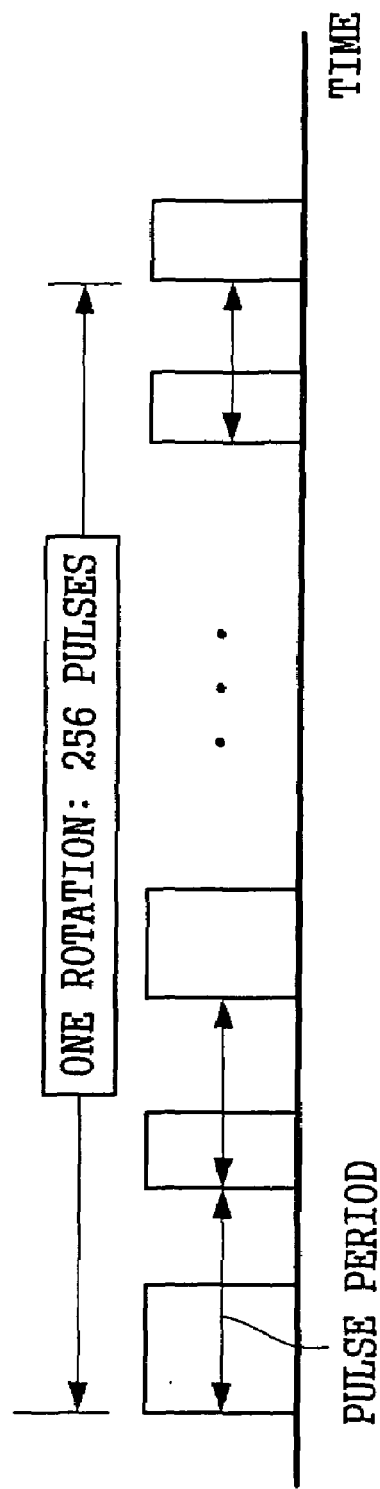

Here, in determining the actual rotational speed, each time a pulse is generated, the period thereof, e.g., as shown in FIG. 16B, the interval between the rising edges or the falling edges, is measured. The total sum of the pulse periods of one rotation (256 pulses) is divided by 256 so as to obtain the average pulse period. By multiplying a predetermined constant by the reciprocal of this period, the average value of the tire rotational speed (the average wheel speed) can be determined.

However, in the present embodiment, it suffices to be able to determine the change rate of the rotational speed of the tire, and there is no need to determine the rotational speed itself of the tire. Therefore, the change rate of the rotational speed of the tire is determined approximately by the formula: change rate of pulse period=pulse period/average pulse period In next step 44, a predetermined higher-order component of the speed change rate of each pulse period is determined. Namely, the speed change rate of each pulse period is Fourier transformed with respect to a rotational angle $2\theta$. In this way, the amplitude ($\delta c+\delta s$) of the speed change rate expressed by formula 7, i.e., the differential phase shift amount, is determined. This differential phase shift amount corresponds to the "characteristic amount" which varies in accordance with the positional offset of the axle. Note that present step 44 corresponds to the higher-order component computing device.

Figure 7:
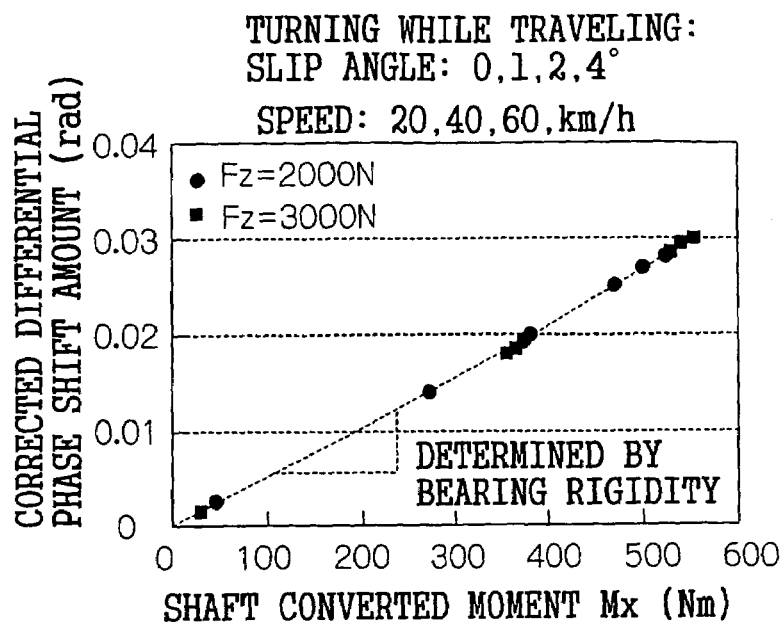
FIG. 7 is a graph showing the relationship between differential phase shift amount and moment.

The relationship between the differential phase shift amount and the moment is determined as shown in FIG. 7 by, for example, making two vehicles having different vehicle weights turn while traveling at various traveling speeds, and measuring, by a predetermined testing device, the differential phase shift amount and the moment Mx caused by the lateral force applied to the axle, and plotting the differential phase shift amount with respect to the moment Mx. Note that FIG. 7 illustrates an example in which vehicle weights Fz were 2000 N and 3000 N, and the speed of each was varied to 20, 40, 60 (km/h). As can be understood from this example, the relationship between the differential phase shift amount and the moment Mx is determined by the "bearing stiffness of the axle".

Figure 8:
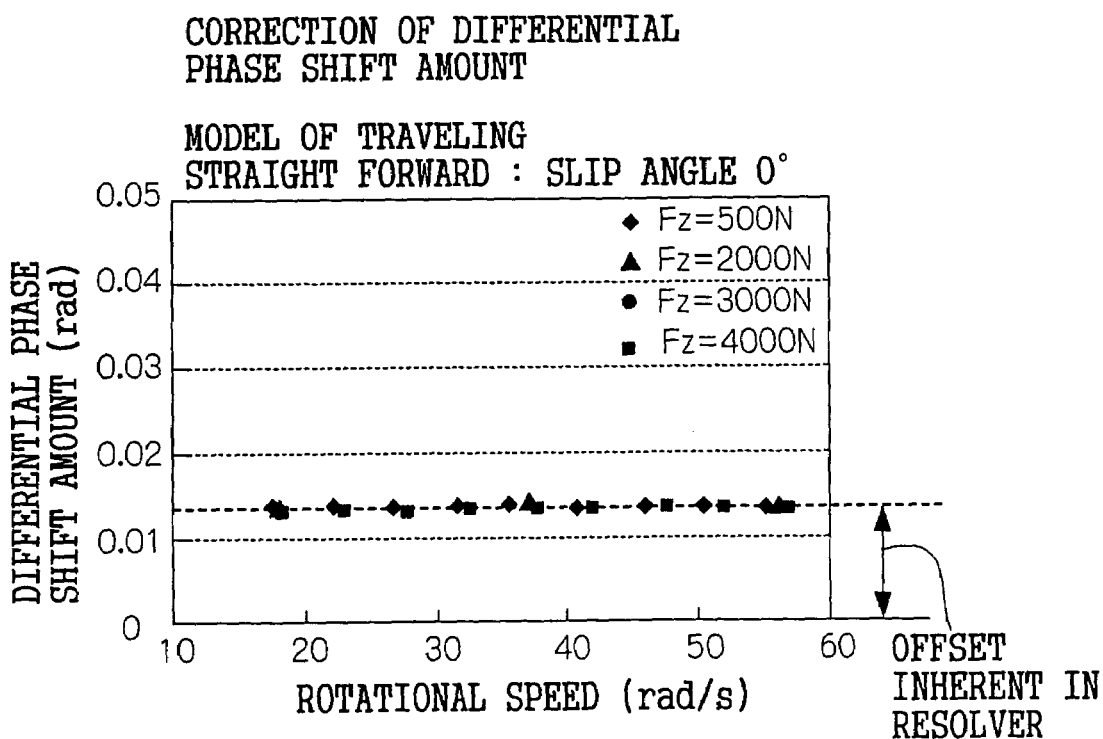
FIG. 8 is a diagram for explanation of an amount of offset of a differential phase shift amount inherent in the resolver.

Note that, in the example of FIG. 7, a value which is corrected as follows is used as the differential phase shift amount which is shown on the vertical axis. Namely, when the differential phase shift amount is determined in a state in which no lateral force is being applied to the axle, as shown in FIG. 8, the differential phase shift amount does not become 0, but rather, has a given value. This is because a differential phase shift amount (an amount of offset inherent in the resolver) arises due to the machining accuracy and the like of the resolver 12. Accordingly, a corrected differential phase shift amount can be obtained by subtracting the amount of offset from the differential phase shift amount which is actually determined. Note that if there is a map or the like which expresses the relationship between the differential phase shift amount and the moment Mx, no problems arise even if the correction of subtracting the amount of offset is not carried out.

In the present embodiment, as described above, the relationship between the moment and the differential phase amount of offset which is the characteristic amount is stored in advance by a map or the like. In step 46, by using this relationship which is stored in advance, the moment is detected from the differential phase shift amount obtained in step 44.

Figure 9A:
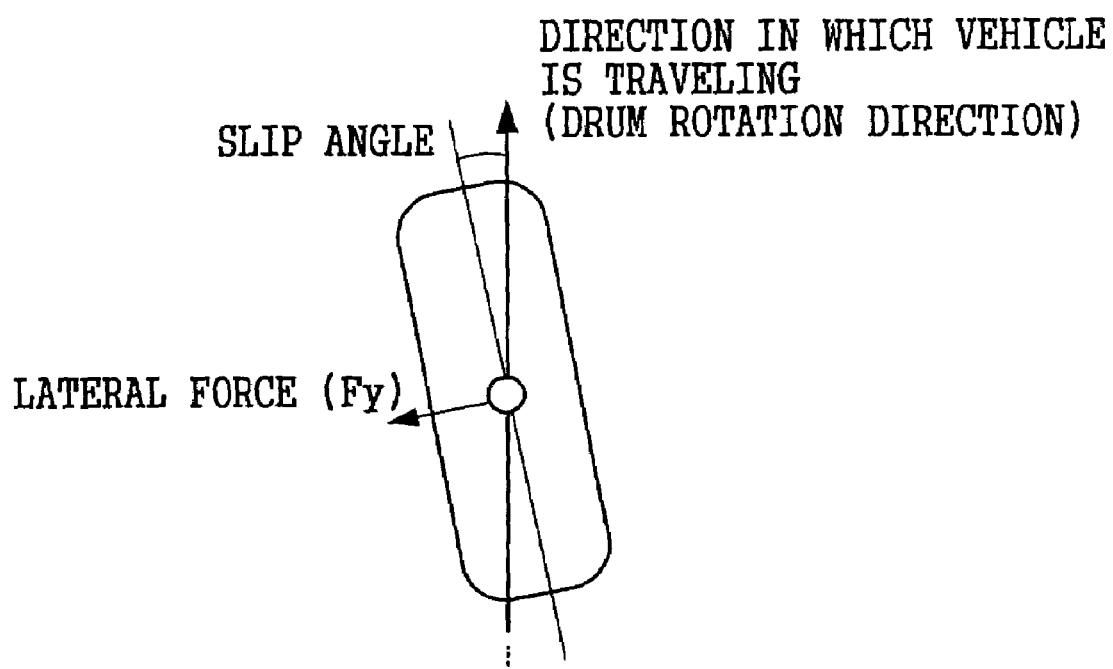
FIGS. 9A and 9B are diagrams showing the relationship between moment and lateral force which is one tire generated force.
Figure 9B:
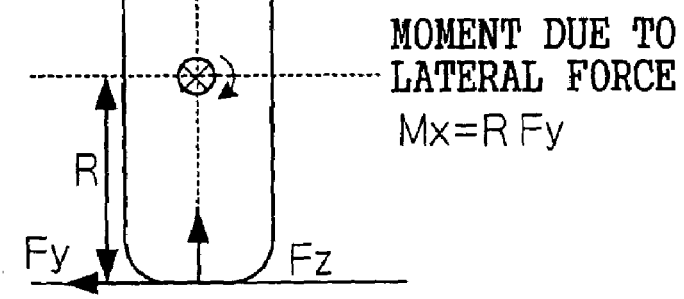

Then, in step 48, a tire generated force is computed from the obtained moment and information regarding the tire mechanisms. For example, as shown in FIG. 9, the moment Mx due to lateral force is given by the product of tire radius R and lateral force Fy. Therefore, the lateral force Fy can be computed by dividing the moment Mx obtained in step 46 by the tire radius R.

The results of computing the moment due to a lateral force actually applied to the axle, by using the tire generated force detecting apparatus which relates to the present embodiment and is described above, are as follows.

Figure 10A:
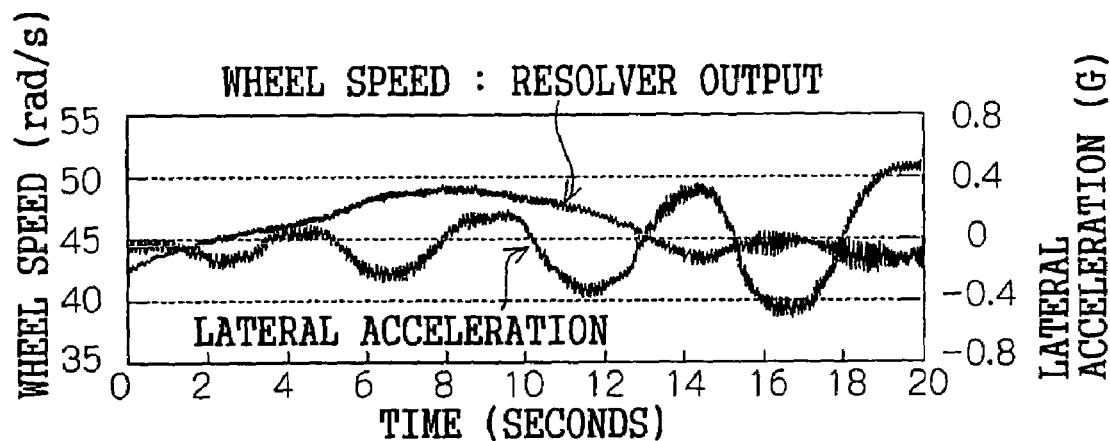
FIG. 10A is a graph showing the relationship between lateral acceleration, wheel speed, and the resolver signal at the time when the vehicle is slaloming, which are the results of an experiment of the present embodiment.
Figure 10B:
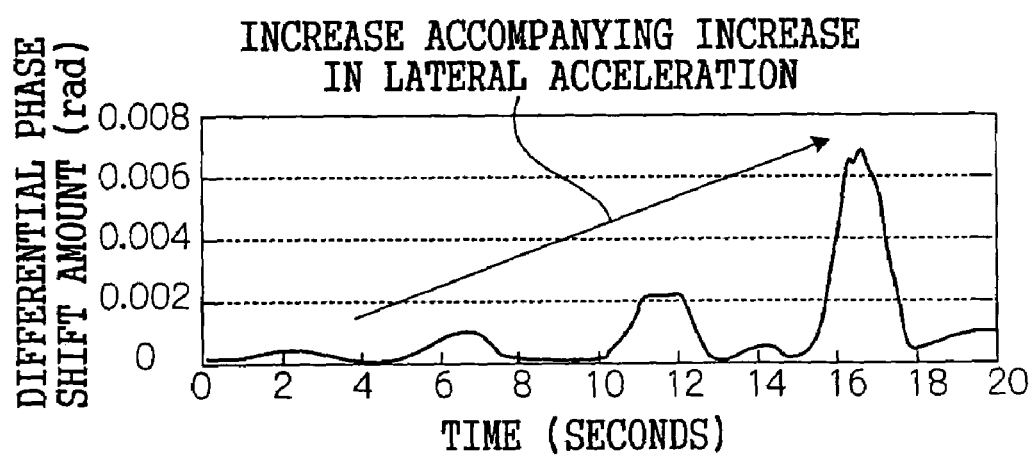
FIG. 10B is a graph corresponding to the graph of FIG. 10A and showing changes over time in the differential phase shift.

As shown in FIGS. 10A and 10B, when a test vehicle to which the resolver was mounted slalomed, as the lateral acceleration increased, the amplitude of the signal outputted from the resolver (the wheel speed signal) increased, and the differential phase shift amount increased. Here, by using the relationship determined in advance between the corrected differential phase shift amount and the moment (the axle converted moment) (i.e., by using the relationship shown in FIG. 11A), the shaft converted moment was determined from the detected differential phase shift amount. Note that the axle converted moment is a moment in which the value of the sensor mounted to the wheel is converted to a moment which is applied to the bearing. In FIG. 11B, the changes over time in the obtained shaft converted moment are shown by the dotted line. From this figure, it can be understood that the moment (estimated values) computed by using the tire generated force computing apparatus corresponds extremely well to the actually measured values shown by the solid line.

As described above, in the present embodiment, the moment is computed on the basis of the amount of positional offset of the axle. Therefore, the moment can be detected highly accurately. Accordingly, a tire generated force also can be detected with high accuracy from the detected moment. Namely, it is possible to provide a moment detecting apparatus and a tire generated force detecting apparatus which are very reliable.

In particular, in the present embodiment, the differential phase shift amount, which is unrelated to the rotational speed of the tire, is detected as the characteristic amount which varies in accordance with the amount of positional offset of the axle, and the moment is computed from this differential phase shift amount. Therefore, the moment can be detected highly accurately.

Further, in the present embodiment, the resolver, which is mainly structured by coils and a core, is used in the rotation sensor. Therefore, there is the advantage that the sensor portion is difficult to break. Note that the resolver is not limited to having the structure described in the present embodiment, and may be a similar structure which detects voltage in accordance with the rotational angle.

Second Embodiment

Next, a tire generated force detecting apparatus relating to a second embodiment will be described. In the present embodiment, the moment is detected without computing the speed change rate and without carrying out Fourier transformation. Note that, because there are structural portions which are similar to those of the above-described first embodiment, the same portions are denoted by the same reference numerals and description thereof is omitted. Only the portions which are different will be described.

Figure 13:
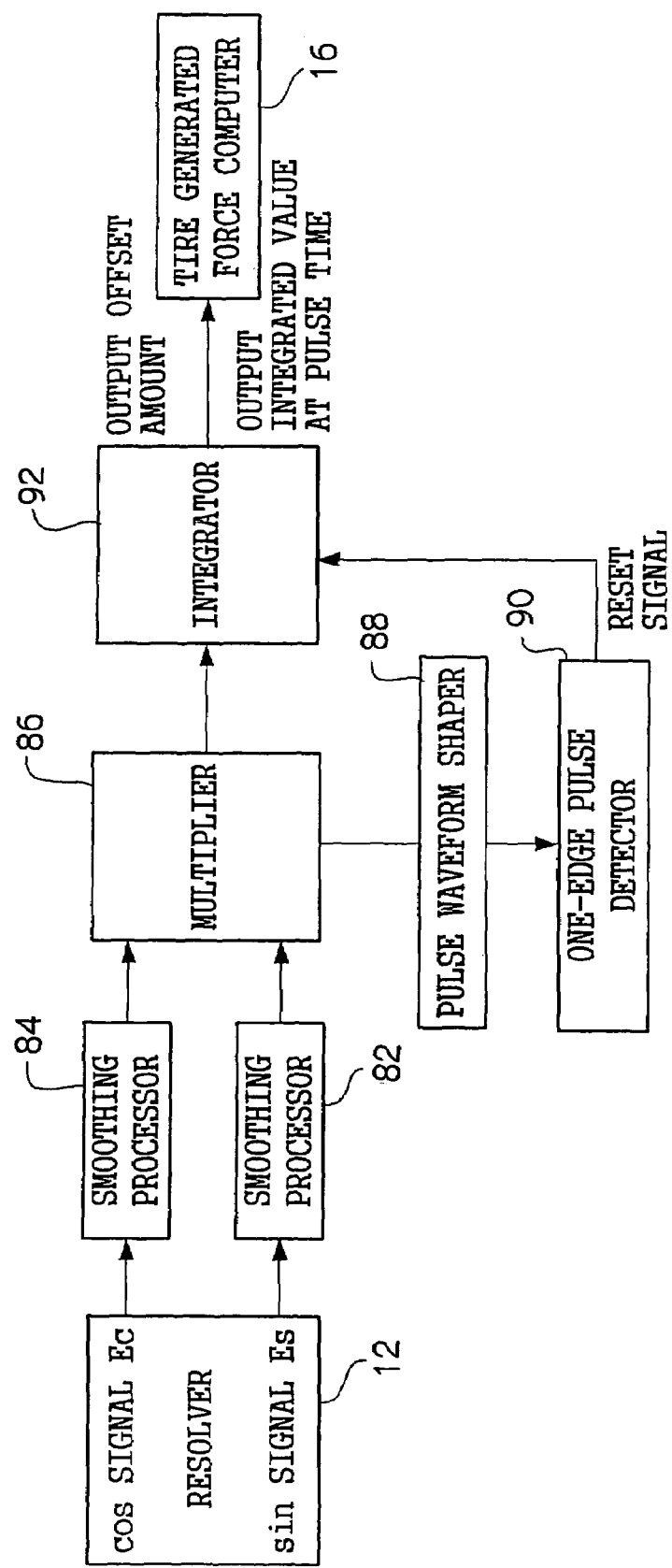
FIG. 13 is a block diagram of a tire generated force computing apparatus relating to a second embodiment.

As shown in FIG. 13, the tire generated force detecting apparatus relating to the present embodiment has, between the resolver 12 and the tire generated force computer 16, a smoothing processor 82 to which the signal Es is inputted and which subjects the signal Es to smoothing processing, and a smoothing processor 84 to which the signal Ec is inputted and which subjects the signal Ec to smoothing processing. The smoothing processors 82, 84 are connected to a multiplier 86 which multiplies the smoothed signal Es and the smoothed signal Ec. Note that a structure may be used in which smoothing processing is carried out after the signal Es and the signal Ec have been multiplied.

A pulse waveform shaper 88 is connected to the multiplier 86. A one-edge pulse detector 90 is connected to the pulse waveform shaper 88. The one-edge pulse detector 90 and the multiplier 86 are connected to input ends of an integrator 92. The output end of the integrator 92 is connected to the tire generated force computer 16.

Next, operation of the present embodiment will be described. However, description of portions which are the same as the operation of the above-described first embodiment will be omitted.

The signals Ec, Es from the resolver 12 are subjected to smoothing processing by the smoothing processor 82 and the smoothing processor 84, respectively. The smoothed signal Es and the smoothed signal Ec are multiplied by the multiplier 86. The product of the output signals Es and Ec of the resolver 12, which is a value obtained by multiplication, is expressed by the following formula.

$$Ec \cdot Es = (KE\sin\omega t)^2 \cos(\theta + \delta_c)\sin(\theta - \delta_s) =$$ Formula 8

$$\frac{1}{2}(KE\sin\omega t)^2\{\sin(2\theta + \delta_c - \delta_s) - \sin(\delta_c + \delta_s)\}$$

FIG. 14 is a graph showing changes in the product (Es·Ec) with respect to the rotational angle θ. As can be understood from this graph and the above formula, the curve sin(2θ+δc−δs) rides on the envelope having an amplitude of ((½(KE sin ωt)²), and an offset of sin(δc+δs) arises. In the same way as the differential phase shift amount (δc+δs), the magnitude of this amount of offset corresponds to the amount of positional offset of the axle. Accordingly, in the present embodiment, this amount of offset is detected as the characteristic amount.

Because smoothing is carried out as described above, the smoothed signal Es and the smoothed signal Ec are multiplied by the multiplier 86, and a signal corresponding to on the aforementioned envelope is determined. When this is averaged for one period, the aforementioned amount of offset is determined. The processing for this averaging is carried out by integrating, over one period, the signal obtained by the multiplication by the multiplier 86.

The timing of this one period is determined as follows. Namely, a pulse waveform, in which a rise and a fall switch, is shaped by the pulse waveform shaper 88 at the zero cross point of the signal obtained by the multiplication by the multiplier 86. The rise or the fall of the pulse shaped by the pulse waveform shaper 88 is detected by the one-edge pulse detector 90. The signal at this time is inputted to the integrator 92 as an integration reset signal. Accordingly, the integrator 92 integrates, over one period, the signal obtained by the multiplication by the multiplier 86.

In order to determine the aforementioned amount of offset sin(δc+δs), as shown in FIG. 14, the average value ((MAX value+MIN value)/2) of the maximum value (MAX value) and the minimum value (MIN value) of the signal from the multiplier 86 may be determined.

In the present embodiment, the relationship between the amount of offset sin(δc+δs) and the moment is measured in advance, and is stored in the tire generated force computer 16 by a map, a data table, a relational expression, or the like. Accordingly, by using the stored relationship, the tire generated force computer 16 determines the moment from the inputted amount of offset sin(δc+δs), and computes the tire generated force from the obtained moment.

As described above, in the second embodiment, the amount of offset which is the characteristic amount can be determined by multiplying the output signals Ec, Es of the resolver and integrating the value obtained by multiplication over one period. Further, the moment is determined from this amount of offset, and the tire generated force can be determined from the obtained moment.

In this way, in the tire generated force detecting apparatus relating to the present embodiment, because the characteristic amount is the above-described amount of offset, the moment and the tire generated force can be detected by a small amount of computation, without computing the speed change rate and without carrying out Fourier transformation. Moreover, because computation of the speed change rate and Fourier transformation are not carried out, there are the advantages that the response is good even at a slow speed, the accuracy of detection at times of acceleration and deceleration can be maintained, the apparatus is strong with respect to road surface disturbances, and the like.

Third Embodiment

Next, a moment detecting apparatus relating to a third embodiment will be described. In the present embodiment, in place of the resolver which is structured by the rotary transformer and the coils, a rotation sensor is structured by coils and a rotating element having a permanent magnet.

As shown in FIG. 15, the moment detecting apparatus relating to the present embodiment has a rotating element 102, a permanent magnet 104 which is fixed to the rotating element 102 and rotates together with the rotating element 102, a plurality of coils 106 which generate electromotive force by electromagnetic induction with the permanent magnet 104, and a moment computer 108 which computes a moment. In the present example, two coils 106A and 106B having the same structure are provided.

The rotating element 102 is mounted to a tire which is a rotating body, so as to rotate together with the tire. The coils 106A, 106B are wound around a fixed element 100 which is fixed to the vehicle body. The coils 106A and 106B are disposed at predetermined positions on an imaginary axis which passes through the rotational center of the tire and extends in the vertical direction of the tire (hereinafter, this imaginary axis is called the "imaginary axis in the tire vertical direction"), so as to together form an angle of 180° with respect to the rotational center of the tire and such that the values of the induced voltages generated thereat are equal.

One end of the coil 106A is connected to one end of the coil 106B, and the other end of the coil 106A and the other end of the coil 106B are connected to the moment computer 108, such that the positive/negative orientations of the induced voltages generated at the coils 106A, 106B are reversed. Note that the coils 106A, 106B correspond to the signal generating devices of the present invention, and generate signals whose magnitudes vary periodically in accordance with the rotational state of the tire and the change in the position of the axle which causes positional offset when lateral force or the like is applied. The detailed operation of the signal generating devices will be described later.

Next, operation of the present embodiment will be described.

When the rotating element 102 rotates accompanying the permanent magnet 104, induced voltages V1, V2 are generated at the two coils 106A, 106B by electromagnetic induction with the permanent magnet 104. As described above, the coils 106A, 106B are connected such that the positive/negative orientations of the induced voltages generated thereat are reversed. Therefore, the voltage at the output end is differential voltage Vd (=V2−V1) of the induced voltages V1, V2 generated at the coils 106A, 106B.

In a case in which no positional offset arises at the axle which is the rotating shaft, the gap (distance) between the rotating element 102 mounted to the tire and the fixed element 100 mounted to the vehicle body does not change, and the gaps between the permanent magnet 104 and the coils 106A, 106B also do not change. Accordingly, the induced voltages V1, V2 are the same values, and the differential voltage Vd is 0. When positional offset of the axle arises, the gaps between the permanent magnet 104 and the coils 106A, 106B change. In this way, the respective magnetic resistances change, and changes arise in the induced voltages generated at the coils 12B1, 12B2.

For example, if the axle shifts toward the coil 106A side, the gap at the coil 106A side becomes small, the magnetic resistance decreases, and the induced voltage V1 becomes greater than the induced voltage V2. As a result, the differential voltage Vd is no longer 0, and a voltage which is equal to this difference is outputted. The amplitude of this differential voltage Vd varies in accordance with the amount of positional offset of the axle. Namely, in the present embodiment, the amplitude of the differential voltage Vd corresponds to the "characteristic amount" which varies in accordance with the positional offset of the axle.

The relationship between the amplitude of the differential voltage Vd and the moment is measured in advance and is stored in the moment computer 108 in a memory (not illustrated) or the like by a map, a data table, a relational expression or the like. The moment computer 108 computes the moment from this relationship which is stored in advance and the amplitude of the inputted differential voltage Vd.

As described above, in the present embodiment, because the moment is computed on the basis of the amount of positional offset of the axle, the moment can be detected with high accuracy. Accordingly, the tire generated force also can be detected with high accuracy from the detected moment. Namely, it is possible to provide a moment detecting apparatus and a tire generated force detecting apparatus which are very reliable.

Moreover, in the present embodiment, in the same way as the resolver, because the rotation sensor is structured by the coils and the core, it is difficult for the sensor portion to break. Note that, in place of the electromagnetic induction type rotation sensor, it is possible to use a rotation sensor using the properties of a semiconductor element such as the Hall effect, or to use a rotation sensor having the property that the output thereof varies in accordance with the strength of magnetic flux.

Fourth Embodiment

Next, a fourth embodiment of the present invention will be described. The tire generated force detecting apparatus relating to the fourth embodiment is equipped with the moment detecting apparatus of the present invention. Further, in the present embodiment, the moment is detected without computing the speed change rate (i.e., without uniformity computation) and without carrying out Fourier transformation. Note that portions which are the same as those of the previously-described embodiments are denoted by the same reference numerals, and description thereof is omitted.

Figure 17:
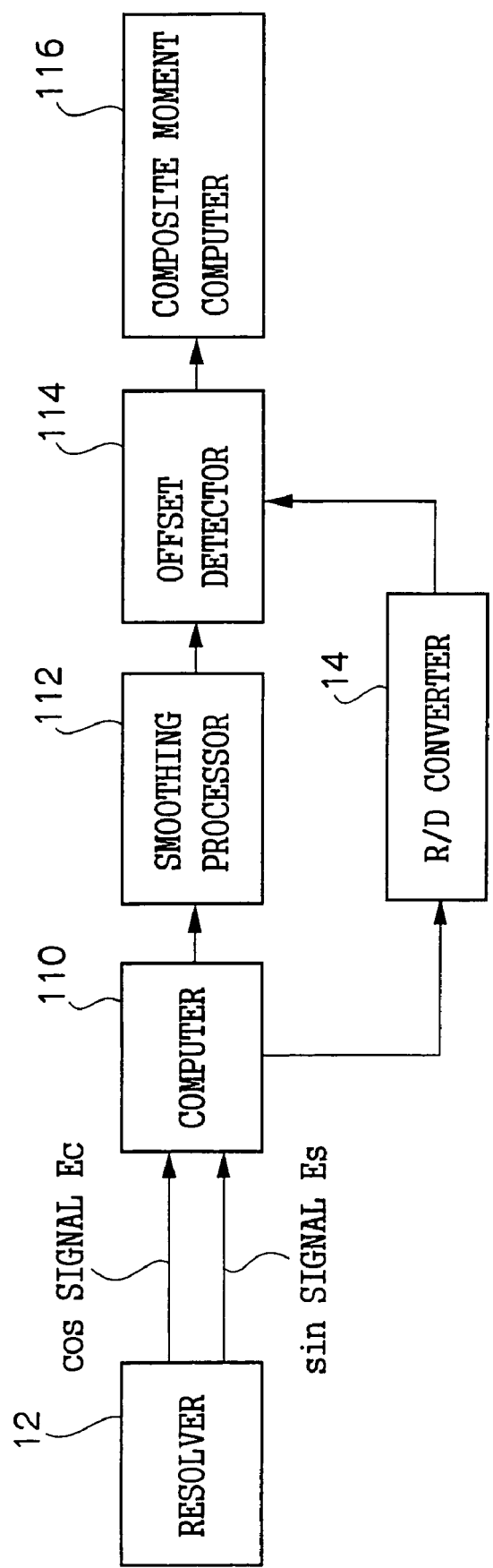
FIG. 17 is a block diagram of a tire generated force computing apparatus relating to a fourth embodiment.

As shown in FIG. 17, the tire generated force detecting apparatus relating to the present embodiment has the resolver 12 which is an electromagnetic induction type rotation sensor, the R/D converter 14 connected to the resolver 12, an offset detector 114 connected to the R/D converter 14, and a composite moment computer 116 connected to the offset detector 114.

A computer 110 and a smoothing processor 112 are disposed between the resolver 12 and the offset detector 114. The computer 110 computes the product of (i.e., multiplies) the input signals Ec, Es from the resolver 12. The smoothing processor 112 smoothes the signal which is inputted from the computer 110, and outputs an amplitude Ep of the signal which has been smoothed.

From the amplitude Ep of the smoothed signal inputted from the smoothing processor 112 and the digital output angle φ inputted from the R/D converter 14, the offset detector 114 detects the amplitude Ep in the case in which the digital output angle φ is a predetermined angle, and, from the amplitude Ep, detects the amount of offset as the "characteristic amount". Further, the composite moment computer 116 computes the moment from the amount of offset detected by the offset detector 114.

Note that the composite moment is a moment in which the moment Mx due to the lateral force and a self-aligning torque Mz are vector-synthesized.

Here, the principles of detecting the amount of offset as the characteristic amount will be described.

The amplitude Ep of the product of the signals Ec, Es from the resolver 12 (i.e., the amplitude Ep of the smoothed signal) is:

$$E_p = \frac{1}{2}\{\sin(2\theta + \delta_c - \delta_s) - \sin(\delta_c + \delta_s)\} \quad \text{Formula 9}$$

The digital output angle φ is:

$$\phi = \theta + \frac{1}{2}\{(\delta_c - \delta_s) - (\delta_c + \delta_s)\cos 2\theta\} \quad \text{Formula 10}$$

Figure 18A:
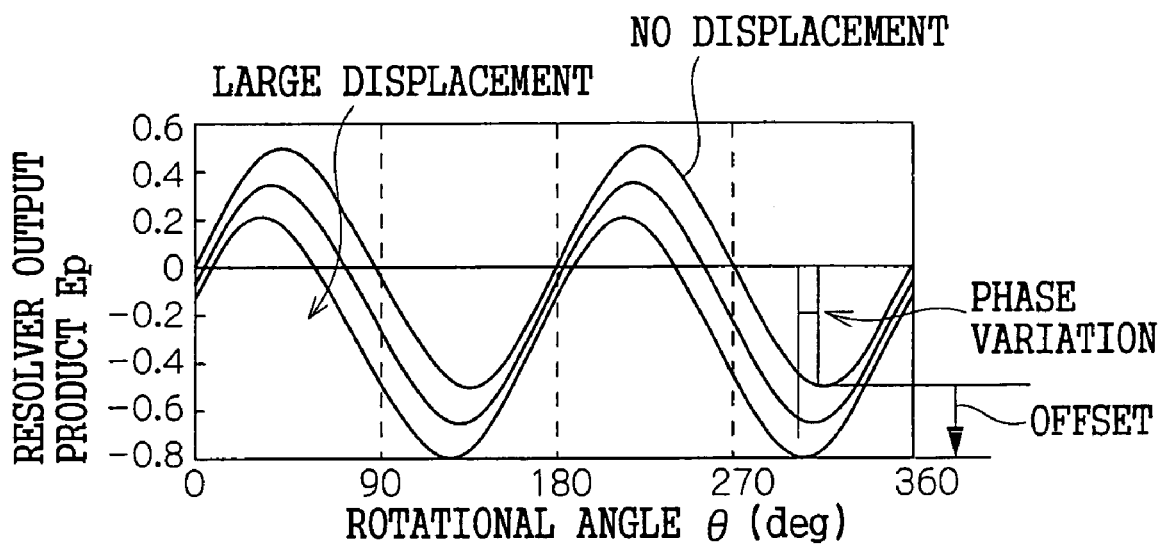
FIG. 18A is a graph showing the relationship between an actual rotational angle of a tire (a so-called actual value) and amplitude of a resolver output product.
Figure 18B:
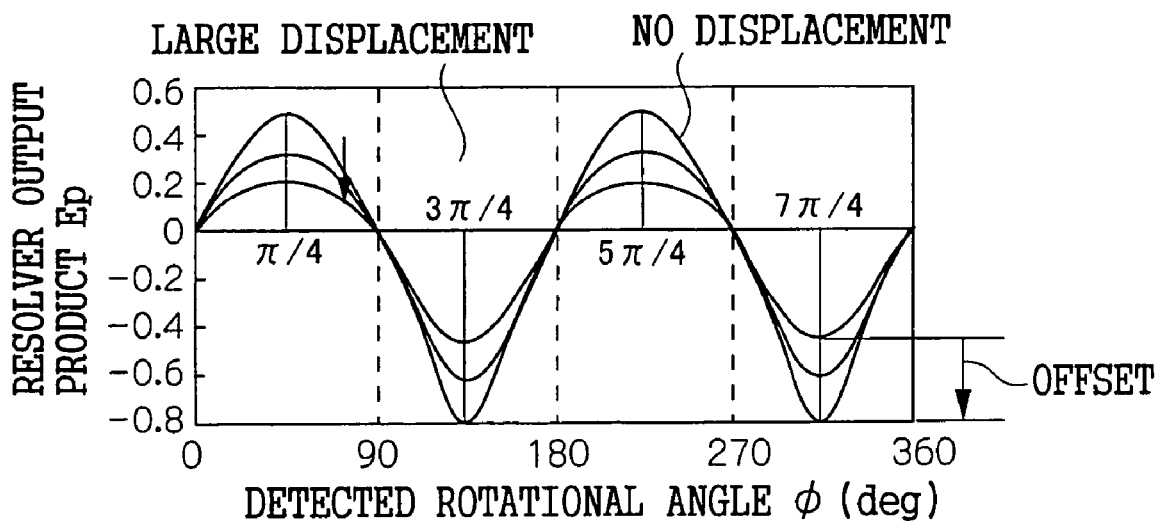
FIG. 18B is a graph showing the relationship between a tire rotational angle detected by using the resolver and amplitude of the resolver output product, including an error caused by the shaft being offset.

As shown in FIG. 18B, when the digital output angle (detected rotational angle) φ is a predetermined angle, the amplitude (resolver output product) Ep has a peak point (a point which is a maximum amplitude). Due to the value, which is obtained by differentiating formula 9 by θ (the rotational angle of the tire (actual value)) at the peak point of the amplitude Ep, being 0, the following formula is established.

$$\cos(2\theta + \delta_c - \delta_s) = 0 \quad \text{Formula 11}$$

Solving the above formula, the following formula is obtained:

$$2\theta + \delta_c - \delta_s = \frac{\pi}{2} + n\pi \quad \text{Formula 12}$$

When this is arranged with respect to θ and substituted into formula 10, the following formula is obtained:

$$\phi = \frac{\pi}{4} + \frac{n}{2}\pi \mp \frac{1}{2}(\delta_c + \delta_s)\sin(\delta_c - \delta_s) \quad \text{Formula 13}$$

−: n is an even number

+: n is an odd number

Under the condition that δc, δs<<1, the above formula is approximated as per the following formula.

$$\phi = \frac{\pi}{4} + \frac{n}{2}\pi \quad \text{Formula 14}$$

The digital output angle φ expressed by formula 14 corresponds to the aforementioned predetermined angle, and is a rotational angle which is approximately considered to be the rotational angle of the tire (the rotating body) when the amplitude Ep is a peak value. Note that, hereinafter, the digital output angle φ expressed by formula 14 will be called the "approximate peak angle" for convenience.

FIG. 18A shows the relationship between the amplitude Ep and the rotational angle (actual value) θ of the tire. As shown in FIG. 18A, when the rotating shaft is offset, the peak position of the amplitude Ep (the rotational angle) is offset in accordance with the amount of offset. Namely, with the rotational angle θ on the horizontal axis, the phase of the amplitude Ep varies in accordance with the amount of offset of the rotating shaft.

In contrast, as shown in FIG. 18B, with the digital output angle φ on the horizontal axis, the phase of the resolver output product Ep is fixed, and the position of the peak point does not fluctuate. Namely, when the digital output angle φ is a predetermined angle, the amplitude Ep has a peak point. The reason why such a difference arises is as follows: as can be understood from formula 10, the digital output angle φ detected by the R/D converter 14 includes a predetermined error other than θ, and due to this error, the phase change corresponding to the amount of offset of the rotating shaft is offset.

Next, operation of the present embodiment will be described.

When the output signals Ec, Es of the resolver 12 are inputted to the computer 110, the computer 110 multiplies the signals Ec, Es so as to compute the product, and outputs the product to the smoothing processor 112. The smoothing processor 112 smoothes the input signal from the computer 110, and outputs the amplitude Ep of the smoothed signal. Namely, the smoothing processor 112 removes the portion relating to sin ωt from the input signal, and outputs the amplitude Ep.

From the amplitude Ep inputted from the smoothing processor 112 and the digital output angle φ inputted from the R/D converter 14, the offset detector 114 detects the amount of offset of the amplitude Ep in a case in which the digital output angle φ is the approximate peak angle. Specifically, the amplitude Ep in a case in which the digital output angle φ is the approximate peak angle at the time when the vehicle is traveling straight forward is determined in advance. The difference between the amplitude Ep when the vehicle is traveling straight forward and the amplitude Ep at the time of detecting the tire generated force is detected as the amount of offset.

Note that, when the aforementioned differential phase shift amount caused by the machining accuracy of the resolver 12 or the like (i.e., the amount of offset inherent in the resolver) is already known, the aforementioned amount of offset (the characteristic amount) may be detected from the amount of offset inherent in the resolver and the amplitude Ep in a case in which the digital output angle φ is the approximate peak angle.

The composite moment computer 116 computes the composite moment from the amount of offset detected by the offset detector 114. Namely, the relationship between the moment and the aforementioned amount of offset (the characteristic amount) which varies in accordance with the positional offset of the axle, is determined in advance. The moment is computed from this relationship and from the amount of offset detected by the offset detector 114.

As described above, in the fourth embodiment, the amplitude Ep of the product of the output signals Ec, Es of the resolver in a case in which the digital output angle φ is the approximate peak angle is detected, and the moment is determined from this amount of offset. Therefore, as compared with a case in which the moment is determined by carrying out computation of the speed change rate or Fourier transformation, the moment can be detected with a small amount of computation.

Moreover, there are various advantages also in a case in which a tire generated force is determined by using the obtained moment. For example, as compared with a case of using the average pulse period of one rotation of the tire, the response can be improved even if the tire is low speed.

When the tire rotates, generally, the rotational speed fluctuates due to unevenness of the tire which is called the tire uniformity. When the speed change rate is determined as in the first embodiment, it cannot be differentiated whether the fluctuations in the rotational speed are due to positional offset of the rotating shaft or are due to the tire uniformity, and such fluctuations are all computed as fluctuations which are due to positional offset of the rotating shaft. In contrast, in the present embodiment, in a case in which the rotational speed fluctuates due to tire uniformity, looking at each time within one period, the amplitude Ep fluctuates due to this. However, there is no effect on the amplitude Ep in a case in which the digital output angle φ is the approximate peak angle. Accordingly, in the present embodiment, the moment which is applied to the tire rotating shaft can be determined accurately without being affected by the tire uniformity.

Further, a case in which the speed change rate is determined as in the first embodiment presupposes that the rotational speed of the tire is constant during one period. Therefore, the aforementioned moment cannot be determined accurately at times of acceleration and deceleration. In contrast, in the present embodiment, the aforementioned moment can be determined accurately even at times of acceleration and deceleration.

Moreover, in the present embodiment, the amplitude Ep can be either a positive or a negative value. Therefore, the direction of the moment can be known from the sign thereof.

Fifth Embodiment

Next, a fifth embodiment of the present invention will be described. The tire generated force detecting apparatus relating to the fifth embodiment is equipped with the moment detecting apparatus of the present invention. Further, in the present embodiment, a moment Mz around an imaginary axis in the vertical direction of the tire, and a moment Mx around an imaginary axis in the horizontal direction of the tire are detected separately. Note that portions which are the same as those of the above-described embodiments are denoted by the same reference numerals, and description thereof is omitted.

Figure 19:
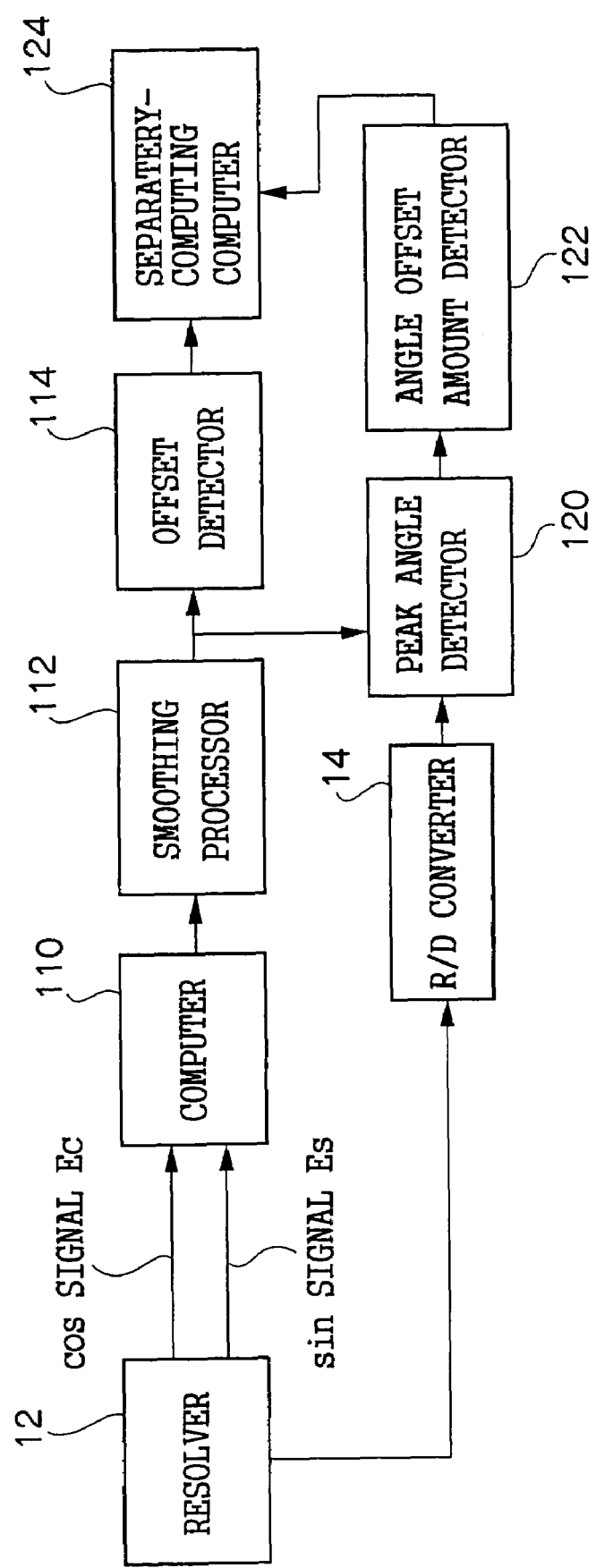
FIG. 19 is a block diagram of a tire generated force computing apparatus relating to a fifth embodiment.

As shown in FIG. 19, the tire generated force detecting apparatus relating to the present embodiment is equipped with the resolver 12 which is an electromagnetic induction type rotation sensor, the computer 110 connected to the resolver 12, the smoothing processor 112 connected to the computer 110, the offset detector 114 connected to the smoothing processor 112, and a separately-computing computer 124 connected to the offset detector 114.

Further, the R/D converter 14 is connected to the resolver 12. The R/D converter 14 is connected to the separately-computing computer 124 via a peak angle detector 120 and an angle offset amount detector 122. The peak angle detector 120 is also connected to the smoothing processor 112.

The peak angle detector 120 detects the accurate value of the digital output angle φ expressed by formula 13 at the time when the amplitude Ep is a peak value (i.e., detects the peak angle), from the smoothed amplitude Ep inputted from the smoothing processor 112 and from the digital output angle φ inputted from the R/D converter 14. The angle offset amount detector 122 determines the difference between the peak angle detected by the peak angle detector 120 and the approximate peak angle expressed by formula 14 (i.e., determines the angle offset amount). On the basis of the amount of offset detected by the offset detector 114 and the angle offset amount detected by the angle offset amount detector 122, the separately-computing computer 124 separately computes the moment around the imaginary axis in the horizontal direction of the tire and the moment around the imaginary axis in the vertical direction (the self-aligning torque).

Figure 20:
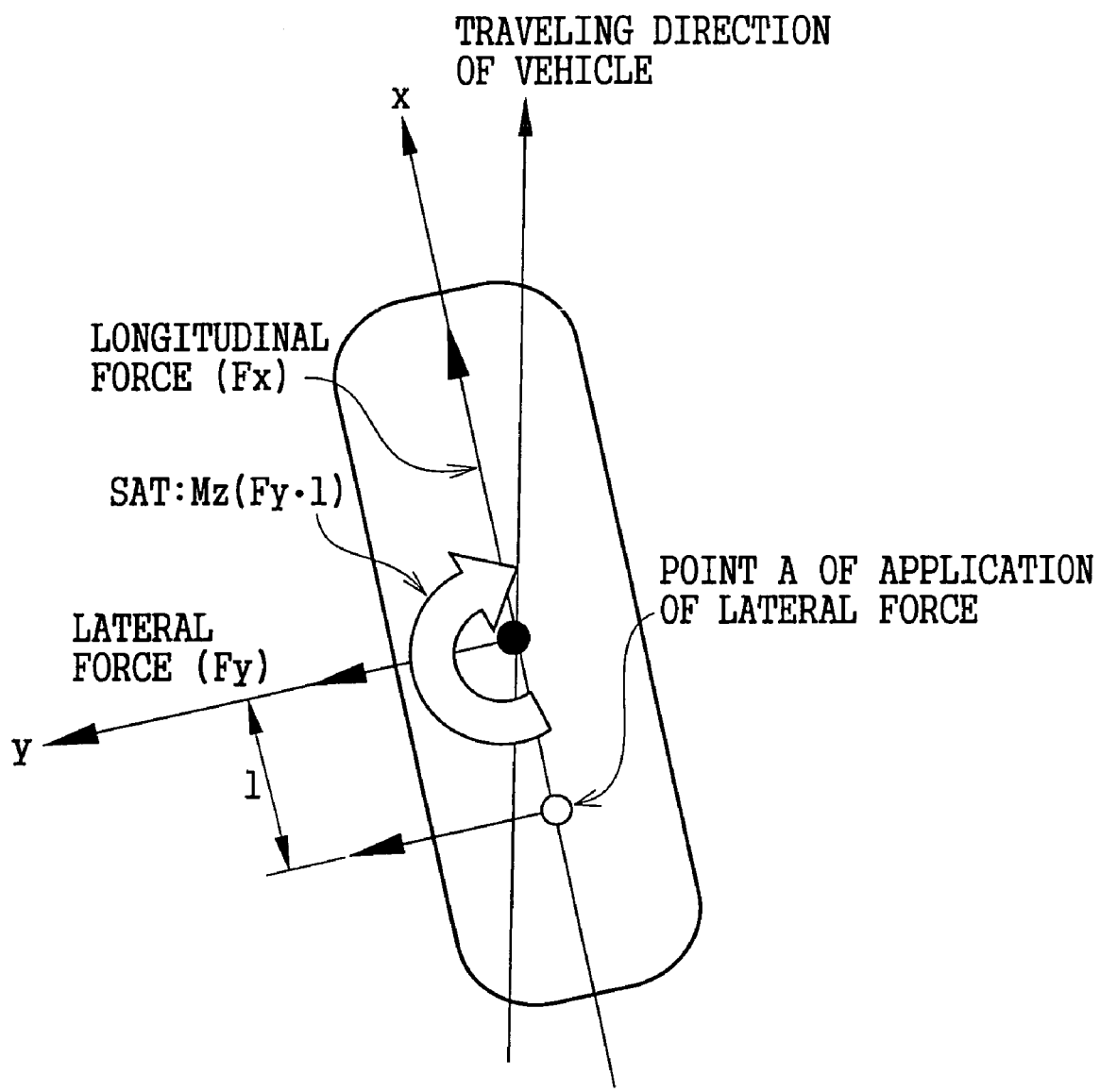
FIG. 20 is an explanatory diagram of moment around an imaginary axis existing within a plane which is perpendicular to a tire rotating shaft.

Here, the moment around the imaginary axis in the horizontal direction of the tire and the moment around the imaginary axis in the vertical direction will be described with reference to FIG. 20. FIG. 20 is a diagram of viewing, from above, a tire of a vehicle in the midst of a turn toward the left.

As shown in FIG. 20, let the position of the tire rotating shaft be the origin, the direction in which the vehicle travels be the x-axis, and the axial direction of the tire be the y-axis. When the steering wheel is turned toward the left for example and the tire is rotated toward the left with respect to the direction in which the vehicle is traveling, lateral force Fy is applied in the direction of the y-axis. However, the actual point A of application of the lateral force is positioned on the ground contact surface of the tire at a position which is offset from the position of the tire rotating shaft (the origin) by a distance 1 in the horizontal direction and a distance R in the vertical direction, i.e., which is offset by a distance Rt (=(1$^2$+R$^2$)$^{1/2}$) from the position of the tire rotating shaft.

In this way, because the point A of application of the lateral force is offset from the position of the tire rotating shaft, a composite moment of the moment (self-aligning torque) Mz, which attempts to return the traveling direction of the tire to the direction in which the vehicle is traveling, and the moment Mx, which attempts to rotate the tire with the traveling direction of the tire being the axis of rotation, is applied to the tire rotating shaft. The moment Mz is a moment around a z-axis which is perpendicular to the aforementioned x-axis and y-axis, and therefore, can be called a moment around an imaginary axis in the vertical direction of the tire. Further, as described above, the moment Mx is a moment around the x-axis which is the tire traveling direction, and therefore, can be called a moment around an imaginary axis in the horizontal direction of the tire.

Note that, in the case in which the point A of application of the lateral force is offset by the distance Rt from the position of the tire rotating shaft, the magnitude of the composite moment applied to the tire rotating shaft is expressed by the product (Rt×Fy) of the distance Rt from the position of the tire rotating shaft and the lateral force Fy.

Next, operation of the present embodiment will be described.

When the output signals Ec, Es of the resolver 12 are inputted to the computer 110, the computer 110 multiplies the signals Ec, Es so as to compute the product, and outputs the product to the smoothing processor 112. The smoothing processor 112 smoothes the input signal from the computer 110, and outputs the amplitude Ep.

The peak angle detector 120 detects the aforementioned peak angle from the amplitude Ep of the smoothed signal inputted from the smoothing processor 112 and from the digital output angle φ inputted from the R/D converter 14. The angle offset amount detector 122 determines a difference $\Delta_1$ (the angle offset amount) between the peak angle which is expressed by formula 13 and detected by the peak angle detector 120, and the approximate peak angle expressed by formula 14. Namely, the difference $\Delta_1$ expressed by the following formula is determined.

$$\Delta_1 = \mp \frac{1}{2}(\delta_c + \delta_s)\sin(\delta_c - \delta_s) \qquad \text{Formula 15}$$

In the same way as in the fourth embodiment, the offset detector 114 detects an amount of offset $\Delta_{off}$ of the amplitude Ep in a case in which the digital output angle φ is the approximate peak angle, from the amplitude Ep of the smoothed signal inputted from the smoothing processor 112 and from the digital output angle φ inputted from the R/D converter 14. Note that, under the condition that δs, δc<<1, sin(δc+δs) is approximated to (δc+δs)

$$\Delta_{off} = -\frac{1}{2}\sin(\delta_c + \delta_s) = -\frac{1}{2}(\delta_c + \delta_s) \qquad \text{Formula 16}$$

On the basis of the amount of offset $\Delta_{off}$ detected by the offset detector 114 and the angle offset amount $\Delta_1$ detected by the angle offset amount detector 122, the separately-computing computer 124 separately computes the moment Mx around the imaginary axis in the horizontal direction of the tire and the moment Mz around the imaginary axis in the vertical direction. Hereinafter, details of the method of computation will be described.

First, the separately-computing computer 124 divides the angle offset amount $\Delta_1$ by the amount of offset $\Delta_{off}$, and determines $\Delta_1/\Delta_{off}$ of the following formula. Note that, under the condition that δs, δc<<1, sin(δc−δs) is approximated to (δc−δs).

$$\Delta_1/\Delta_{off} = \pm\sin(\delta_c - \delta_s) = \pm(\delta_c - \delta_s) \qquad \text{Formula 17}$$

Solving the above formula, δs, δc are expressed by the following equations. In the present embodiment, the phase offset amounts δs, δc correspond to the "characteristic amounts".

$$\delta_s = \mp \frac{2\Delta_{off} + \Delta_1/\Delta_{off}}{2} \qquad \text{Formula 18}$$

$$\delta_c = \mp \frac{2\Delta_{off} - \Delta_1/\Delta_{off}}{2}$$

−: n is an even number
+: n is an odd number

Figure 21:
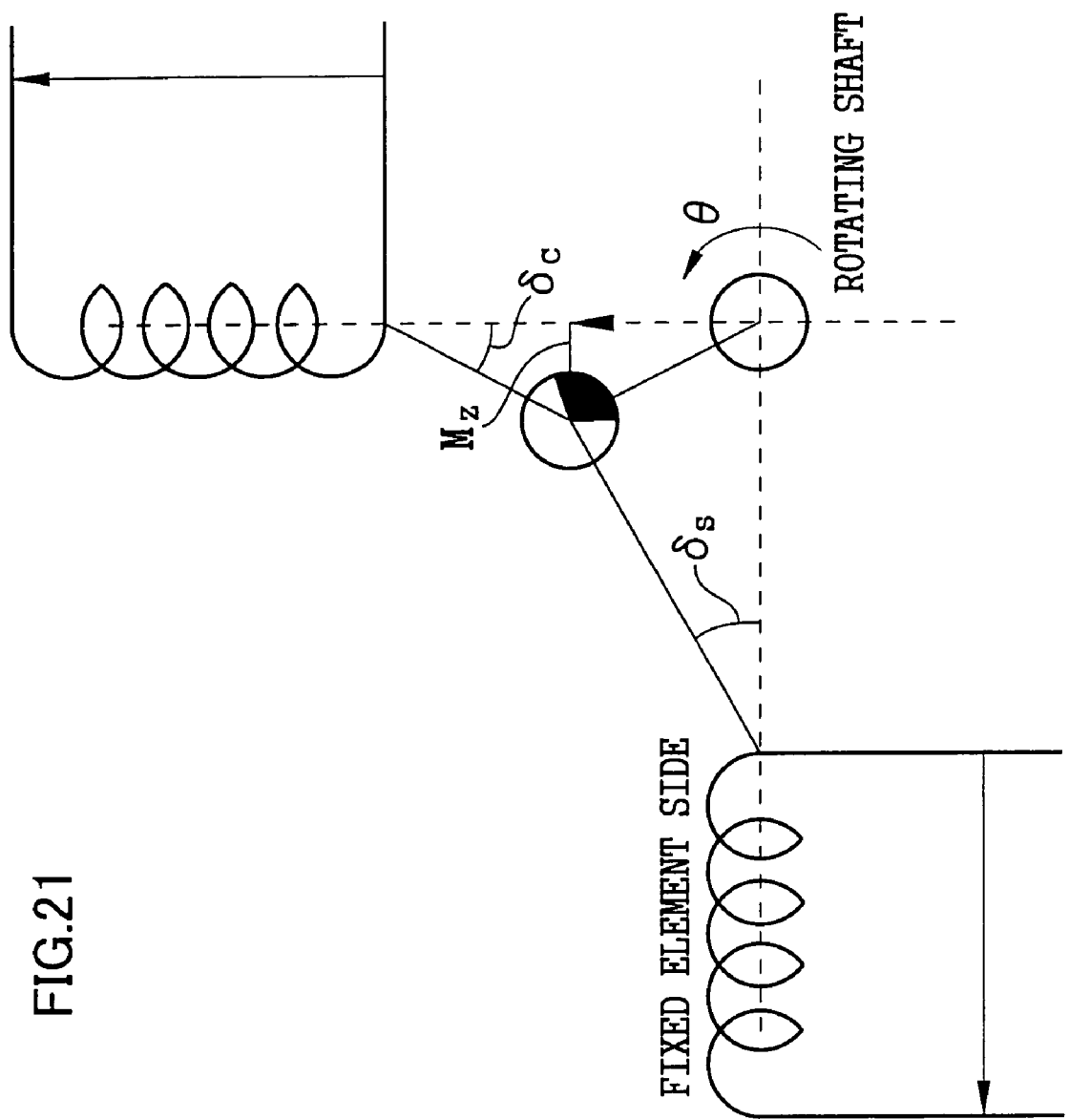
FIG. 21 is a diagram showing the relationship of correspondence among δs, δc, a moment Mz around an imaginary axis in a vertical direction of the tire, and a moment Mx around an imaginary axis in a horizontal direction of the tire.

As explained in FIG. 5, δs, δc are the amounts of offset of the phases which are generated by the induced voltages of the coils 12B1, 12B2 of the resolver 12 in a case in which the position of the rotating shaft is offset by γ. A moment corresponding to the amount of offset γ is applied to the rotating shaft of the tire. When δs, δc<<1, as shown in FIG. 21, δc corresponds to the moment Mz around the imaginary axis in the vertical direction of the tire, and δs corresponds to the moment Mx around the imaginary axis in the horizontal direction of the tire.

In the present embodiment, the relationship between δc and the moment Mz and the relationship between δs and the moment Mx are determined in advance and are stored in advance in a memory or the like in the separately-computing computer 124 by maps, data tables, relational expressions, or the like. From the δs, δc determined as described above, the separately-computing computer 124 determines the moment Mz around an imaginary axis in the vertical direction of the tire and the moment Mx around an imaginary axis in the horizontal direction of the tire from the aforementioned stored relationships.

As described above, the conventional structure of merely determining the composite moment is divided in the present embodiment into the moment around an imaginary axis in the horizontal direction of the tire and the moment around an imaginary axis in the vertical direction, and each of the moments can be detected.

Sixth Embodiment

Next, a moment detecting apparatus relating to a sixth embodiment of the present invention will be described. In the present embodiment, a rotation sensor is structured by coils and a rotating element having permanent magnets. Further, comparing the structure of the present embodiment and the structure of the third embodiment, in the third embodiment, only one pair of coils is provided, whereas in the present embodiment, three pairs of coils are provided. Note that portions which are the same as those of the previously-described embodiments are denoted by the same reference numerals, and description thereof is omitted.

Figure 22:
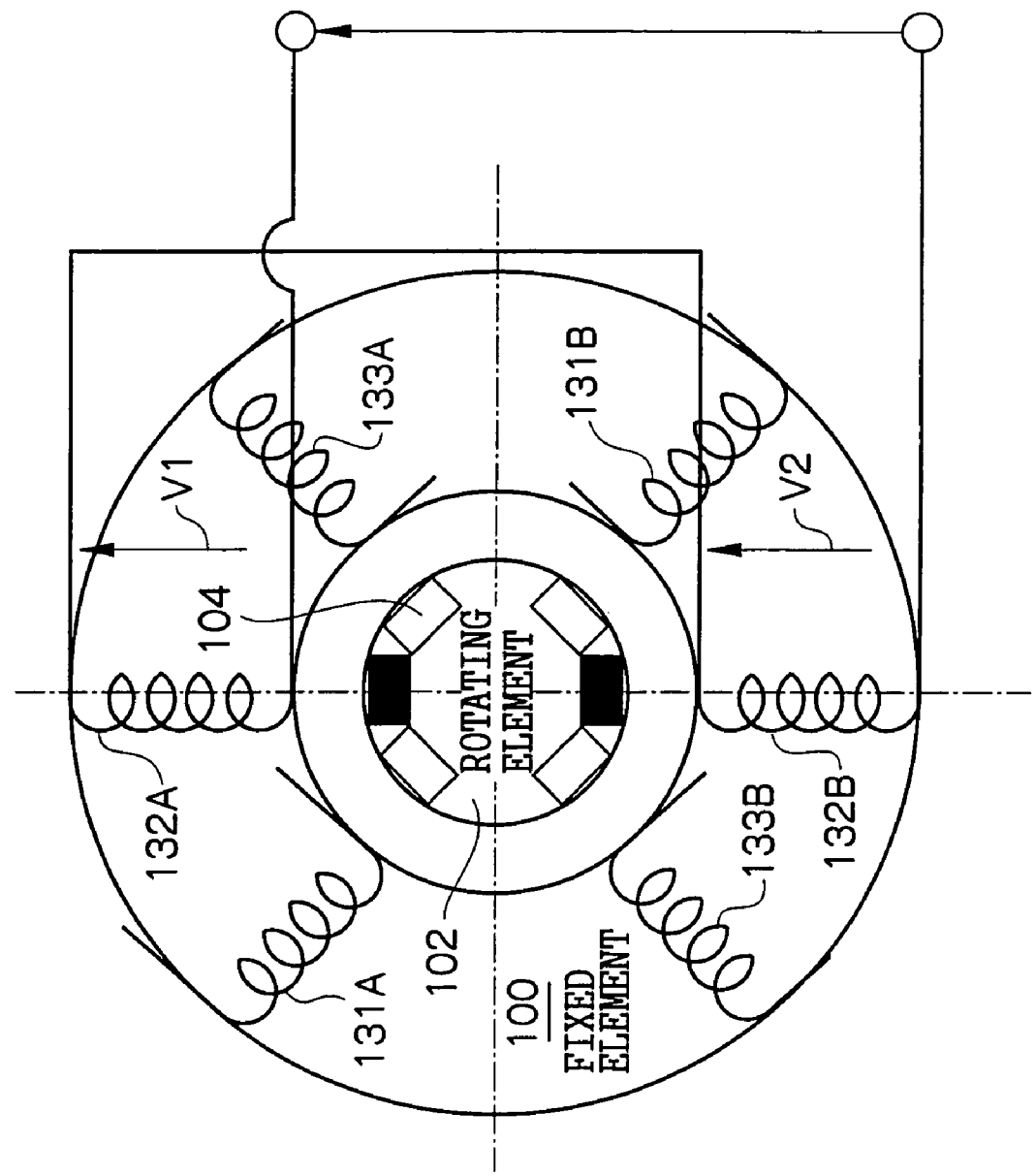
FIG. 22 is a diagram showing the relationship of positions at which coils are disposed in a sixth embodiment.

As shown in FIG. 22, the moment detecting apparatus relating to the present embodiment is equipped with a rotation sensor which is structured by the rotating element 102, the permanent magnets 104 which are fixed to the rotating element 102 and rotate together with the rotating element 102, and a plurality of coils at which electromotive force is generated due to electromagnetic induction with the permanent magnets 104. In the present embodiment, there are provided a first coil pair 131 structured by two coils 131A and 131B having the same structure, a second coil pair 132 structured by two coils 132A and 132B having the same structure, and a third coil pair 133 structured by two coils 133A and 133B having the same structure. Accordingly, three pairs of coils (six coils) are provided.

The rotating element 102 is mounted to the tire which is a rotating body so as to rotate together with the tire. The coils are wound around the fixed element 100 which is fixed to the vehicle body. The two coils which structure a coil pair, e.g., the coils 132A and 132B, are disposed at predetermined positions on an imaginary axis in the vertical direction of the tire, so as together form an angle of 180° with respect to the rotational center and such that the values of the induced voltages generated thereat are equal.

The coil 131A and the coil 133A are disposed with the coil 132A therebetween so as to form a predetermined angle (an electrical angle which is α/2) with the coil 132A at the tire rotational angle with respect to the center of rotation. Similarly, the coil 131B and the coil 133B are disposed with the coil 132B therebetween so as to form a predetermined angle with the coil 132B at the tire rotational angle with respect to the center of rotation. Note that the electrical angle α can be, for example, π/2, but is not limited to this value.

Figure 23:
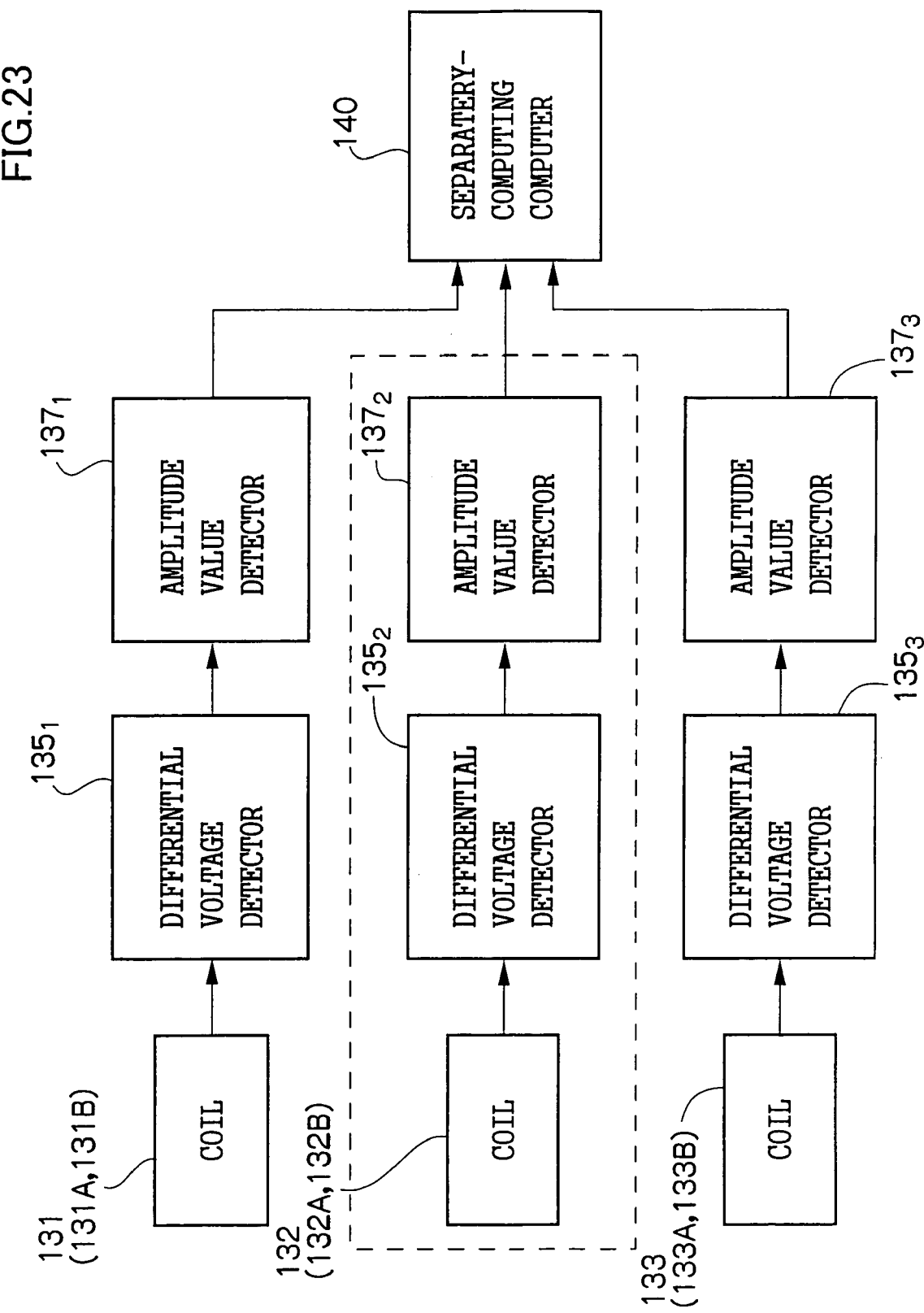
FIG. 23 is a block diagram of a tire generated force computing apparatus relating to the sixth embodiment.

Further, as shown in FIG. 23, the moment detecting apparatus relating to the present embodiment has differential voltage detectors $135_1$ through $135_3$ which are connected to the first coil pair 131, the second coil pair 132, and the third coil pair 133, respectively; amplitude value detectors $137_1$ through $137_3$ which are connected to the differential voltage detectors $135_1$ through $135_3$, respectively; and a separately-computing computer 140 which is connected to the respective amplitude value detectors $137_1$ through $137_3$.

Next, operation of the present embodiment will be described.

The differential voltage detectors $135_1$ through $135_3$ detect the differential voltages of the corresponding coil pairs. Namely, the differential voltage detector $135_1$ detects a differential voltage $V_{d1}$ of the first coil pair 131, the differential voltage detector $135_2$ detects a differential voltage $V_{d2}$ of the second coil pair 132, and the differential voltage detector $135_3$ detects a differential voltage $V_{d3}$ of the third coil pair 133. The amplitude value detectors $137_1$ through $137_3$ detect the amplitude values of the corresponding differential voltages. In the present embodiment, the respective amplitude values of the differential voltages $V_{d1}$, $V_{d2}$, $V_{d3}$ correspond to "characteristic amounts" which vary in accordance with the positional offset of the rotating shaft.

Figures 24A, 24B:
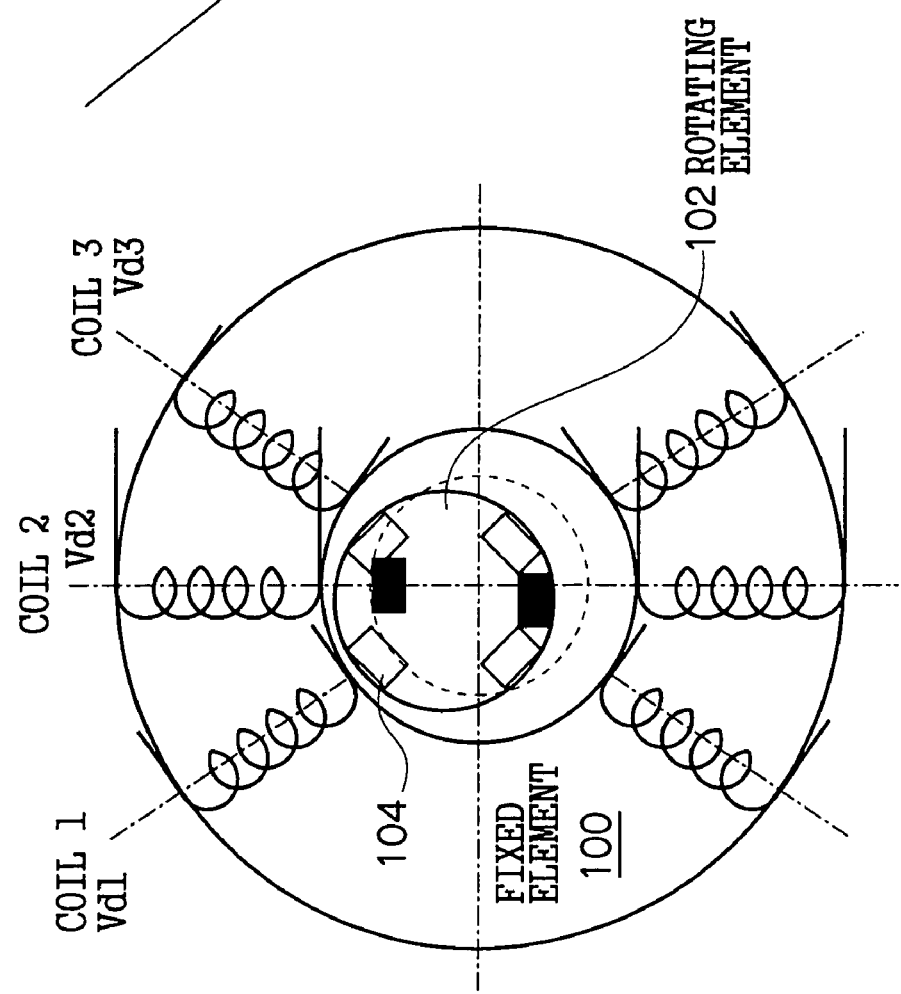
FIG. 24A is a diagram showing the relationship of positions at which coils are disposed.
FIG. 24B is a diagram showing the relationship between moments around imaginary axes existing within planes which are perpendicular to the tire rotating shaft.

As shown in FIG. 22, in a case in which no positional offset of the axle which is the rotating shaft is generated, the gaps between the permanent magnets 104 and the coils do not change, the differential voltages $V_{d1}$, $V_{d2}$, $V_{d3}$ are respectively 0, and the amplitude values thereof are 0. As shown in FIG. 24A, when positional offset of the axle arises, the gaps between the permanent magnets 104 and the coils change. Therefore, changes arise in the induced voltages generated at the respective coils. As a result, the differential voltages $V_{d1}$, $V_{d2}$, $V_{d3}$ are no longer 0, and the amplitude values thereof fluctuate.

The directions of the vectors of the respective generated differential voltages $V_{d1}$, $V_{d2}$, $V_{d3}$ are shown in FIG. 24B. The directions of the vectors of differential voltage $V_{d1}$ and differential voltage $V_{d2}$ are offset by α/2 in terms of the electrical angle. Further, the directions of the vectors of differential voltage $V_{d2}$ and differential voltage $V_{d3}$ also are offset by α/2 in terms of the electrical angle.

As shown in FIG. 24B, the moment Mx around an imaginary axis in the horizontal direction of the tire corresponds to the differential voltage $V_{d2}$. Further, the moment Mx corresponds to the value expressed by the following formula.

$$(V_{d1} + V_{d3})\cos\frac{\alpha}{2} \qquad \text{Formula 19}$$

The moment Mz around an imaginary axis in the vertical direction of the tire corresponds to the value expressed by the following formula.

$$(V_{d1} - V_{d3})\sin\frac{\alpha}{2} \qquad \text{Formula 20}$$

At the separately-computing computer 140, the relationship between the differential voltage $V_{d2}$ (or the value of formula 19) and the moment Mx around an imaginary axis in the horizontal direction of the tire, and the relationship between the value of formula 20 and the moment Mz around an imaginary axis in the vertical direction of the tire, are determined in advance and stored in a memory (not illustrated) or the like by maps, data tables, relational expressions, or the like. By using the amplitude values of the inputted differential voltages $V_{d1}$, $V_{d2}$, $V_{d3}$, the separately-computing computer 140 computes the moment Mz and the moment Mx from the relationships which were stored in advance.

As described above, the conventional structure of merely determining the composite moment is divided in the present embodiment into the moment around an imaginary axis in the horizontal direction of the tire and the moment around an imaginary axis in the vertical direction, and each of the moments can be detected.

Note that, as described above, the moment Mx around an imaginary axis in the horizontal direction of the tire can be determined from the differential voltage $V_{d2}$ or from the value of formula 19. The moment Mx may be determined by either one of these methods, or the moment Mx may be computed by both methods and the average value of the both determined. In a case in which the moment Mx around an imaginary axis in the horizontal direction of the tire is determined from the value of formula 19, it is possible to omit the second coil pair 132 and the differential voltage detecting circuit $135_2$ and the amplitude value detector $137_2$ which correspond to this coil pair 132 (i.e., to omit the portion enclosed by the dashed line in FIG. 23).

The coils 131A and 133A are disposed so as to be offset by the same electrical angle ($\alpha/2$) with respect to the coil 132A. However, the respective coils may be disposed such that the amount of offset of the electrical angle between the coil 131A and the coil 132A is different than the amount of offset of the electrical angle between the coil 133A and the coil 132A.

Seventh Embodiment

Next, a moment detecting apparatus relating to a seventh embodiment will be described. In the present embodiment, a rotation sensor is structured by coils and a rotating element having permanent magnets, and the moment is detected from the phase difference of the induced voltages of the plurality of coils. Note that portions which are the same as those of the previously-described embodiments are denoted by the same reference numerals, and description thereof is omitted.

Figure 25:
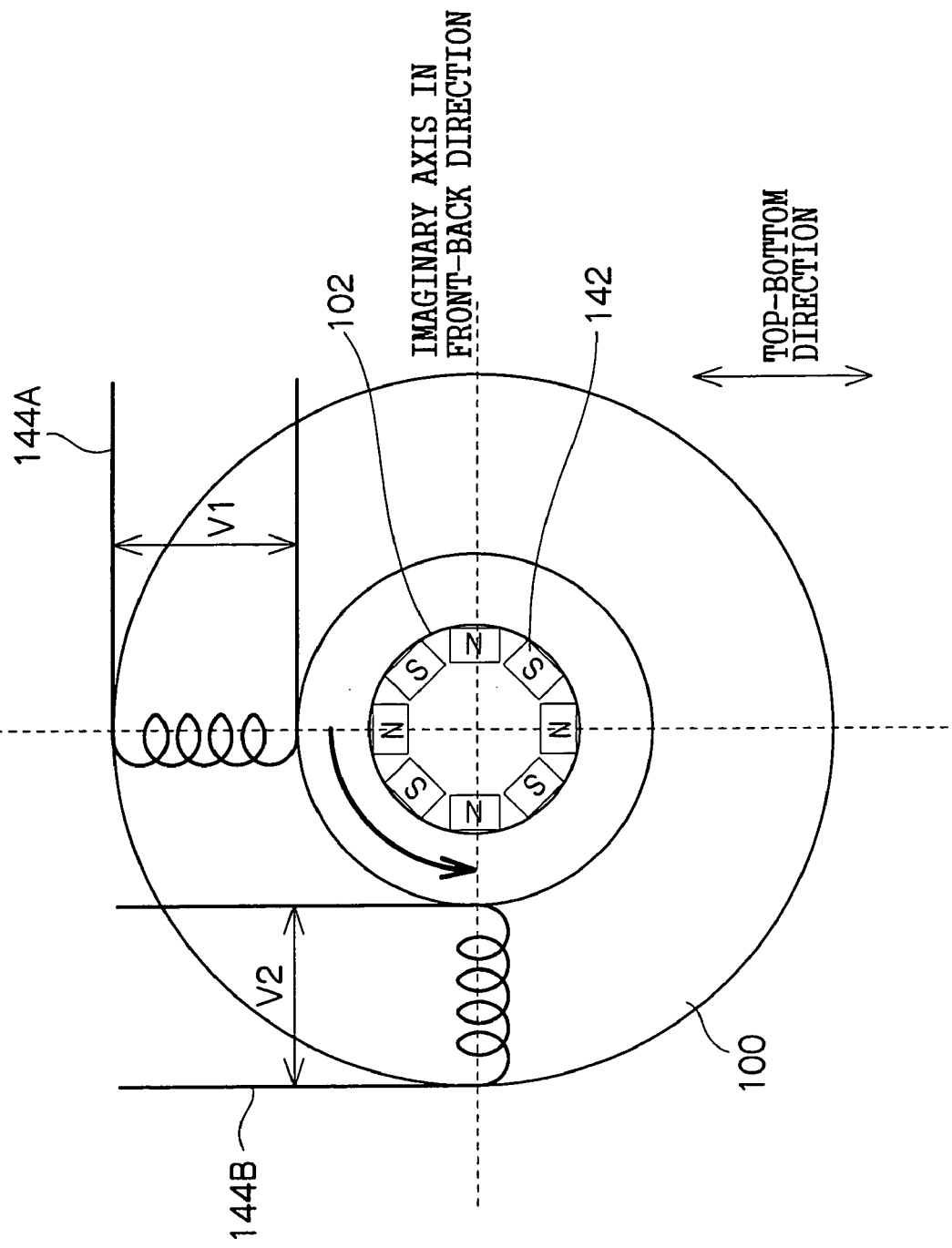
FIG. 25 is a schematic diagram showing the structure of a rotation sensor in a seventh embodiment.

As shown in FIG. 25, the moment detecting apparatus relating to the present embodiment is equipped with a rotational sensor structured by the rotating element 102, a large number of permanent magnets 142 which are fixed to the rotating element 102 and rotate together with the rotating element 102, and a plurality of coils 144 which generate electromotive force due to electromagnetic induction with the permanent magnets 142. In this example, two coils 144A and 144B having the same structure are provided. Further, the large number of permanent magnets 142 are arranged on the outer periphery of the rotating element 102 along the radial direction of the rotating element 102 such that the S magnetic poles and N magnetic poles thereof are arranged alternately. Note that eight permanent magnets are provided in FIG. 25, but the number of permanent magnets is not limited to the same.

The rotating element 102 is mounted to a tire, which is a rotating body, so as to rotate together with the tire. The coils are wound around the fixed element 100 which is fixed to the vehicle body. The coil 144A is disposed on an imaginary axis extending along the vertical direction of the tire. The coil 144B is disposed on an imaginary axis in the horizontal direction of the tire. The imaginary axis in the tire vertical direction and the imaginary axis in the tire horizontal direction are orthogonal to one another. Therefore, the coils 144A and 144B are disposed at predetermined positions so as together form an angle of 90° with respect to the rotational center, and such that the values of the induced voltages generated thereat are equal.

Figure 26:
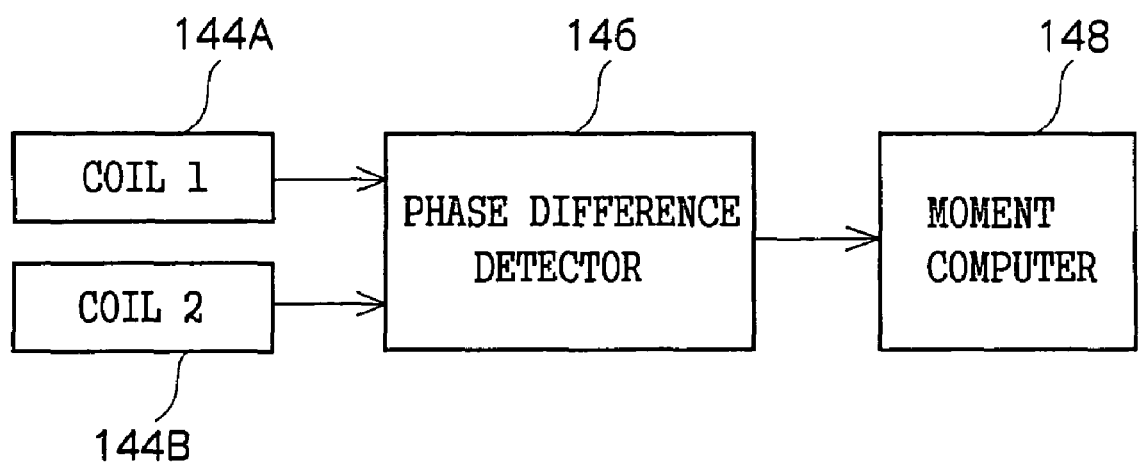
FIG. 26 is a block diagram showing the structure of a moment computing apparatus relating to the seventh embodiment.

As shown in FIG. 26, the moment detecting apparatus relating to the present embodiment has a phase difference detector 146 connected to the coils 144A, 144B respectively, and a moment computer 148 connected to the phase difference detector 146. The phase difference detector 146 detects the phase difference of the induced voltages generated at the coils 144A, 144B. On the basis of the phase difference detected by the phase difference detector 146, the moment computer 148 computes the moment Mx around an imaginary axis in the horizontal direction of the tire. The coils 144A, 144B are connected to the phase difference detector 146 such that the induced voltages generated thereat are detected separately.

Figure 29:
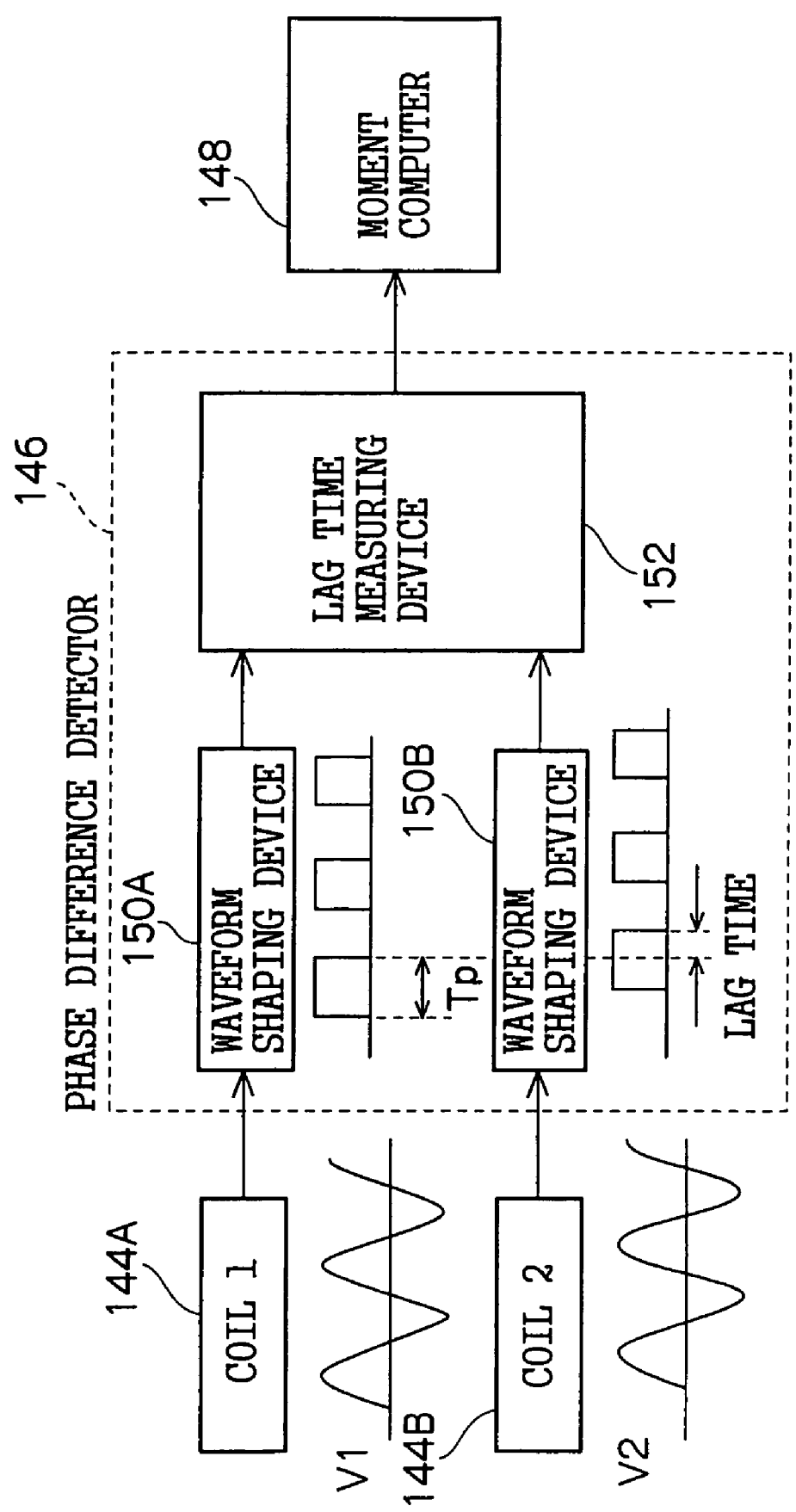
FIG. 29 is a block diagram showing the structure of a phase difference detector in the seventh embodiment.

As shown in FIG. 29, the phase difference detector 146 has waveform shaping devices 150A, 150B provided so as to correspond to the coils 144A, 144B respectively, and a lag time measuring device 152 connected to the waveform shaping devices 150A, 150B respectively. The waveform shaping devices 150A, 150B shape the waveforms of the signals inputted from the corresponding coils into rectangular waves. The lag time measuring device 152 detects the phase difference of the two rectangular waves inputted from the waveform shaping devices 150A, 150B.

Next, operation of the present embodiment will be described.

When the rotating element 102 rotates accompanying the permanent magnets 142, the induced voltages V1, V2 are generated at the two coils 144A, 144B by the electromagnetic induction between the coils 144A, 144B and the permanent magnets 142. The signals V1, V2 are outputted to the phase difference detector 146.

In a case in which no positional offset of the axle which is the rotating shaft is generated, as shown in FIG. 27A, the gaps between the permanent magnets 142 and the coils 144A, 144B do not change. Accordingly, the phase difference of the induced voltages V1, V2 is 0. As shown in FIG. 28, when positional offset of the axle arises, the gaps between the permanent magnets 142 and the coils 144A, 144B change. Changes thereby arise in the phases of the induced voltages generated at the coils 144A, 144B.

For example, as shown in FIG. 28, given that the rotating element 102 rotates in the direction of the arrow, in a case in which the rotating shaft is displaced upwardly, the changes in the polarities (S/N) of the permanent magnets with respect to the coil 144A are constant, but the changes in the polarities of the permanent magnets with respect to the coil 144B are slow. As a result, as shown in FIG. 27B, although the phase of the induced voltage V1 does not change, the phase of the induced voltage V2 is late, and a phase difference arises. Further, in a case in which the rotating shaft is displaced downwardly, the changes in the polarities of the permanent magnets with respect to the coil 144B are fast, and the phase of the induced voltage V2 is advanced such that a phase difference arises. In this way, the phase difference varies in accordance with the amount of positional offset of the rotating shaft. Namely, in the present embodiment, this phase difference corresponds to the "characteristic amount" which varies in accordance with the positional offset of the rotating shaft.

In the present example, in a case in which the rotating shaft is offset in the vertical direction, the induced voltage V1 of the coil 144A, which is disposed on an imaginary axis in the tire vertical direction, does not fluctuate. Therefore, the phase difference is measured by using the phase of the induced voltage V1 as the standard. In a case in which the rotating shaft is offset in the horizontal direction, the induced voltage V2 of the coil 144B, which is disposed on an imaginary axis in the tire horizontal direction, does not fluctuate. Therefore, the phase difference is measured by using the phase of the induced voltage V2 as the standard.

The signal V1 from the coil 144A is inputted to the waveform shaping device 150A, and the waveform of the signal V1 is shaped into a rectangular wave (a pulse wave). Moreover, the signal V2 from the coil 144B is inputted to the waveform shaping device 150B, and the waveform of the signal V2 is shaped into a rectangular wave. The lag time measuring device 152 detects a pulse interval Tp and a time difference ΔTdelay (the phase difference) between the falling edges or the rising edges of the two pulse waves inputted from the waveform shaping devices 150A, 150B, and outputs Tp and ΔTdelay to the moment computer 148. For example, in a case in which the phase of the induced voltage V1 is used as the standard, the lag time of the phase of the induced voltage V2 is measured.

On the basis of the time difference ΔTdelay and the pulse interval Tp which have been detected by the lag time measuring device 152, the moment computer 148 computes the moment Mx around an imaginary axis in the horizontal direction of the tire. Hereinafter, the method of computation will be described in detail.

First, the moment computer 148 divides the time difference ΔTdelay by the pulse interval Tp so as to determine ΔTdelay/Tp. Because the time difference ΔTdelay varies in accordance with the rotational speed of the tire, the time difference ΔTdelay is normalized by being divided by the pulse interval Tp.

Figure 30:
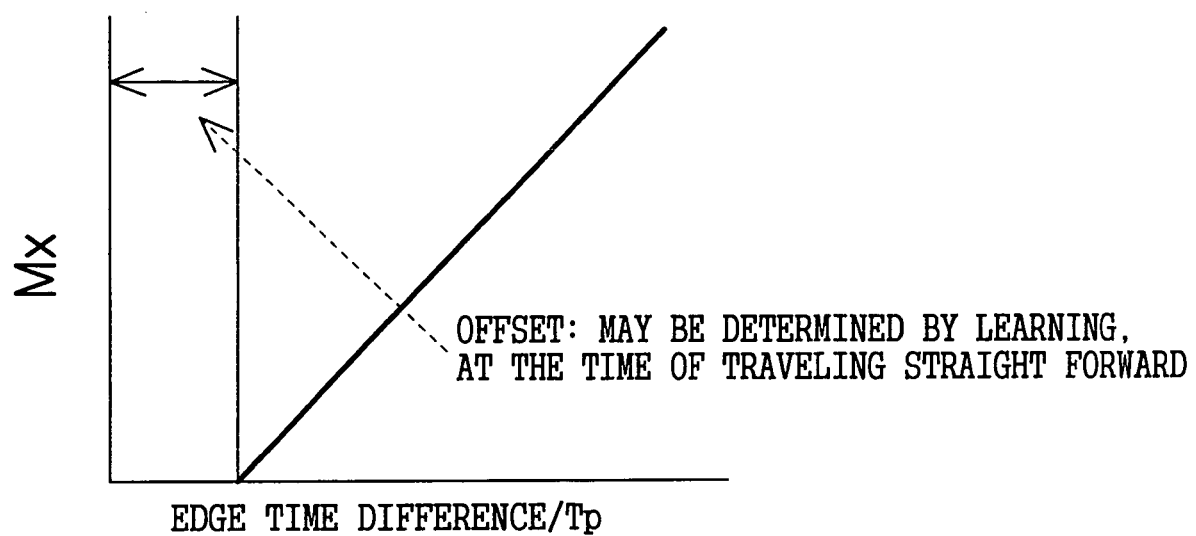
FIG. 30 is a diagram showing a map expressing the relationship between ΔTdelay/Tp and the moment Mx.

The relationship between ΔTdelay/Tp and the moment Mx is measured in advance and is stored in the moment computer 148 in a memory or the like by a map, a data table, a relational expression, or the like. For example, as shown in FIG. 30, the relationship between ΔTdelay/Tp and the moment Mx can be determined in advance and expressed by a map. The moment computer 148 computes the moment Mx from the relationship which is stored in advance and from the value of ΔTdelay/Tp.

Note that, in the example shown in FIG. 30, when ΔTdelay/Tp is determined in a state in which no lateral force is applied to the tire (i.e., when the vehicle is traveling straight forward), ΔTdelay/Tp is not zero and has a given value. This is because an inherent amount of offset arises due to the machining accuracy or the like of the rotation sensor. Accordingly, the inherent amount of offset may be determined in advance, and the value of ΔTdelay/Tp may be corrected by the obtained amount of offset.

As described above, in the present embodiment, the moment is computed on the basis of the amount of positional offset of the axle. Therefore, the moment can be detected highly accurately. Accordingly, the tire generated force also can be detected with high accuracy from the detected moment. Namely, it is possible to provide a moment detecting apparatus and a tire generated force detecting apparatus which are highly reliable.

In particular, in the present embodiment, the phase difference of the induced voltages generated by a pair of coils is detected as the characteristic amount which varies in accordance with the amount of positional offset of the axle, and the moment is computed from this phase difference. Therefore, the moment can be detected with high accuracy.

In the same way as in the third embodiment, there is the advantage that it is difficult for the sensor portion to break. Note that, in place of the rotation sensor utilizing the electromagnetic induction phenomenon, it is possible to use a rotation sensor using the properties of a semiconductor element such as the Hall effect, or the like.

Figure 32:
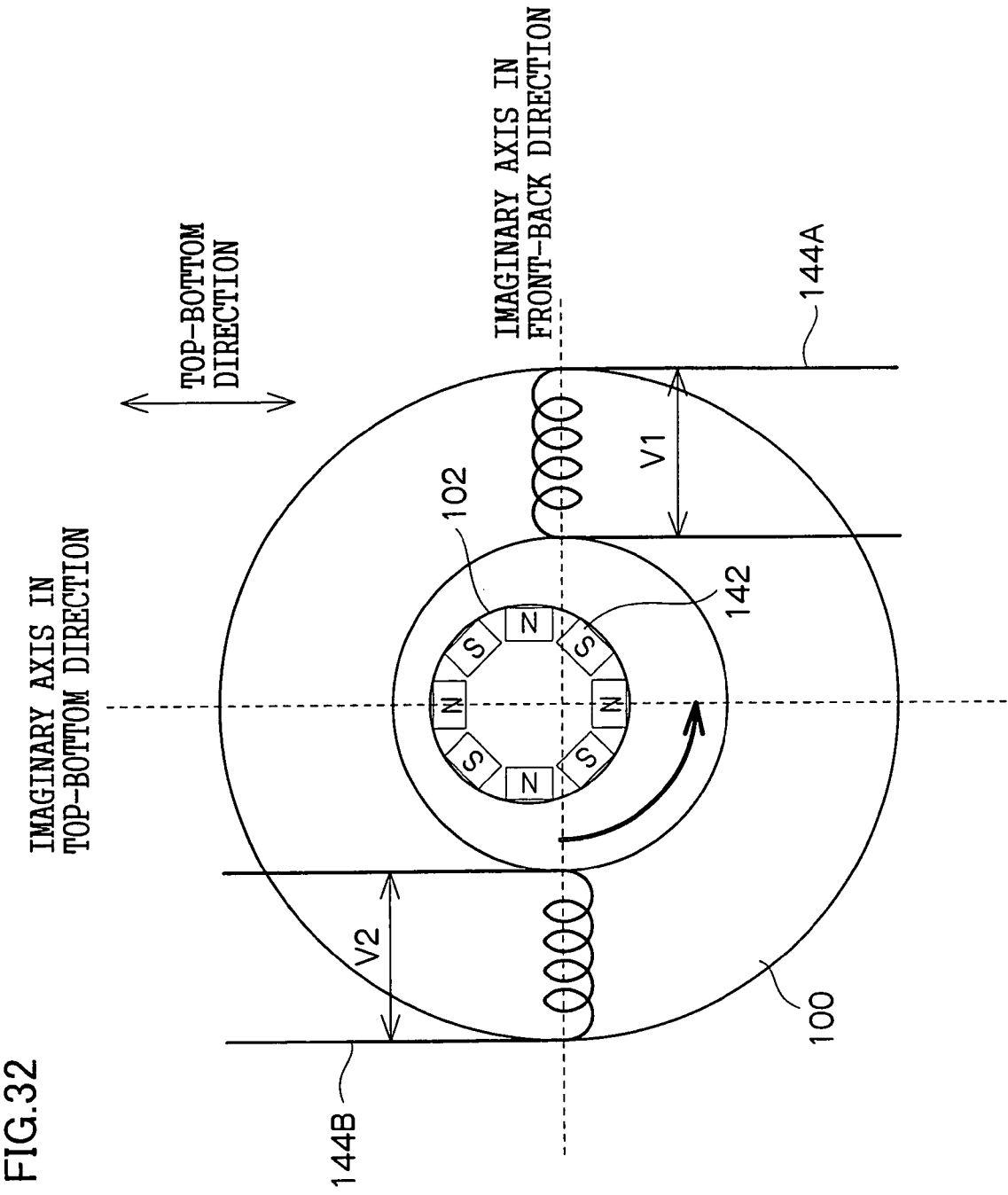
FIG. 32 is a schematic diagram showing the structure of another rotation sensor.

Note that, in the seventh embodiment, the coils 144A and 144B are disposed such that these two coils together form an angle of 90° with respect to the center of rotation. However, the angle at which the coils are disposed is not limited to 90°. For example, as shown in FIG. 32, the coils 144A and 144B may be disposed on an imaginary axis in the horizontal direction of the tire, so as to together form an angle of 180° with respect to the center of rotation. As illustrated, in a case in which the rotating element 102 rotates in the direction of the arrow, when the rotating shaft is offset upwardly, the phase of the induced voltage V1 of the coil 144A advances, and the phase of the induced voltage V2 of the coil 144B lags. In this way, because a phase difference arises between the induced voltages V1, V2, the moment Mx can be detected by using this phase difference as the characteristic amount. However, when the angle at which the coils are disposed is 90°, the sensitivity of detecting the phase difference is highest, and therefore, it is preferable that the two coils be disposed at an angle of 90°.

Eighth Embodiment

Next, a moment detecting apparatus relating to an eighth embodiment will be described. The present embodiment has the same structure as the moment detecting apparatus relating to the seventh aspect, except that the device structure of the phase difference detector is changed. Therefore, portions which are the same are denoted by the same reference numerals, and description thereof is omitted. Only the points which differ will be described.

Figure 31:
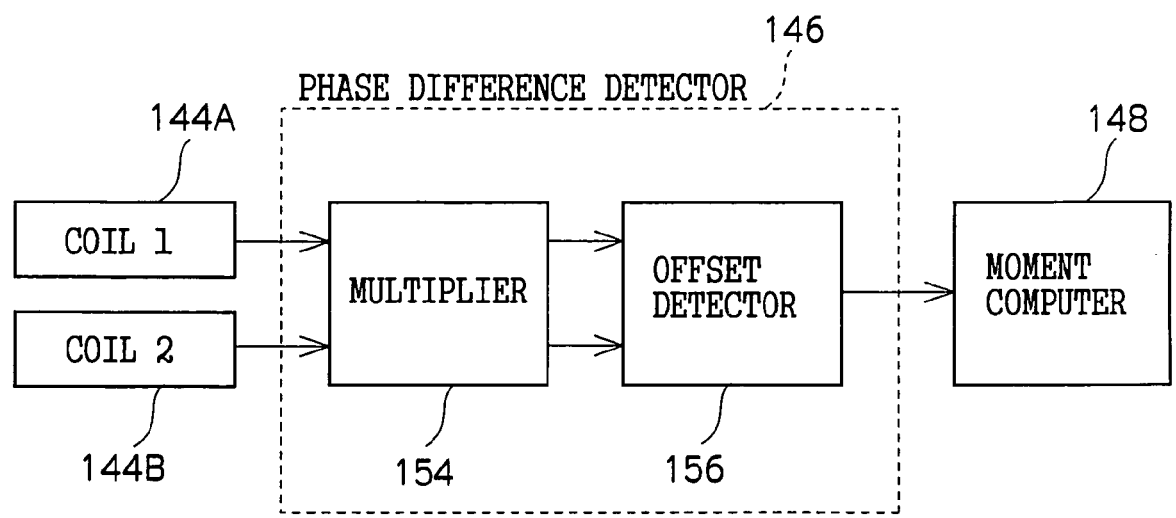
FIG. 31 is a block diagram showing the structure of a phase difference detector in an eighth embodiment.

As shown in FIG. 31, the moment detecting apparatus relating to the present embodiment is equipped with the phase difference detector 146 which is connected to the coils 144A, 144B respectively, and the moment computer 148 which is connected to the phase difference detector 146. The phase difference detector 146 has a multiplier 154 which multiplies the signals V1 and V2 inputted from the coils 144A, 144B, and an offset detector 156 connected to the multiplier 154. The offset detector 156 detects the amount of offset of the signal inputted from the multiplier 154.

Here, the principles of detecting the amount of offset will be described.

Given that the phase difference in a case in which the signal V1 is used as the standard is ψ, the signals V1, V2 from the coils 144A, 144B respectively are as per the following equations.

$$V1 = \sin\theta$$

$$V2 = \sin(\theta - \varphi) \qquad \text{Formula 21}$$

The product of the signals V1, V2 is expressed by the following formula.

$$V1 \cdot V2 = -\frac{1}{2}\cos(\theta - \varphi) + \frac{1}{2}\cos\varphi \qquad \text{Formula 22}$$

As can be understood from the above formula, an offset of ½(cos ψ) arises in the product of the signals V1, V2. This amount of offset corresponds to the phase difference ψ, i.e., the amount of positional offset of the axle. Accordingly, in the present embodiment, this amount of offset is detected as the characteristic amount.

The relationship between the amount of offset ½(cos ψ) and the moment Mx is measured in advance and is stored in the moment computer 148 by a map, a data table, a relational expression, or the like. Accordingly, by using the stored relationship, the moment computer 148 computes the moment from the inputted amount of offset.

As described above, in the present embodiment, the output signals V1, V2 of the two coils are multiplied together, the amount of offset which is the characteristic amount is detected from this value obtained by multiplication, and the moment is determined from the detected amount of offset. Therefore, as compared with a case in which the moment is determined by carrying out computation of the speed change rate or Fourier transformation, the moment and the tire generated force can be detected by a small amount of computation.

Ninth Embodiment

Next, a moment detecting apparatus relating to a ninth embodiment will be described. In the present embodiment, a rotation sensor is structured by coils and a rotating element having permanent magnets. Further, comparing the structure of the present embodiment and the structure of the seventh embodiment, in the seventh embodiment, only one pair of coils is used, whereas in the present embodiment, two pairs of coils are used. Note that portions which are the same as those of the previously-described embodiments are denoted by the same reference numerals, and description thereof is omitted.

Figure 33:
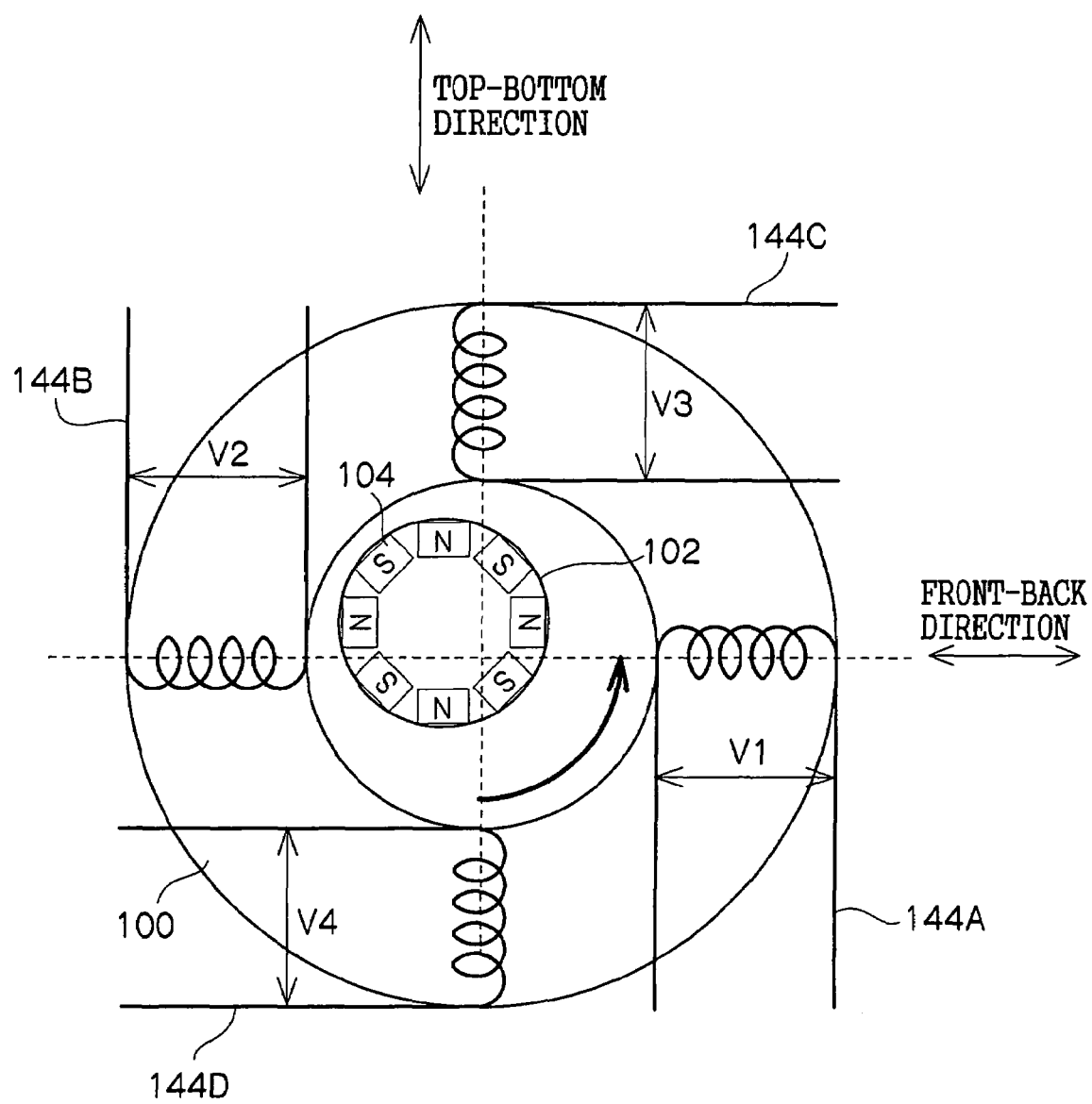
FIG. 33 is a schematic diagram showing the structure of a rotation sensor in a ninth embodiment.

As shown in FIG. 33, the moment detecting apparatus relating to the present embodiment has a rotational sensor at which are provided the four coils 144A, 144B, 144C and 144D having the same structure. The coils 144A and 144B are disposed on an imaginary axis in the tire horizontal direction. The coils 144C and 144D are disposed on an imaginary axis in the tire vertical direction. The imaginary axis in the tire vertical direction and the imaginary axis in the tire horizontal direction are orthogonal to one another. Therefore, the coils 144A and 144B, and the coils 144C and 144D are disposed at predetermined positions so as to together form angles of 90° with respect to the center of rotation.

Figure 34:
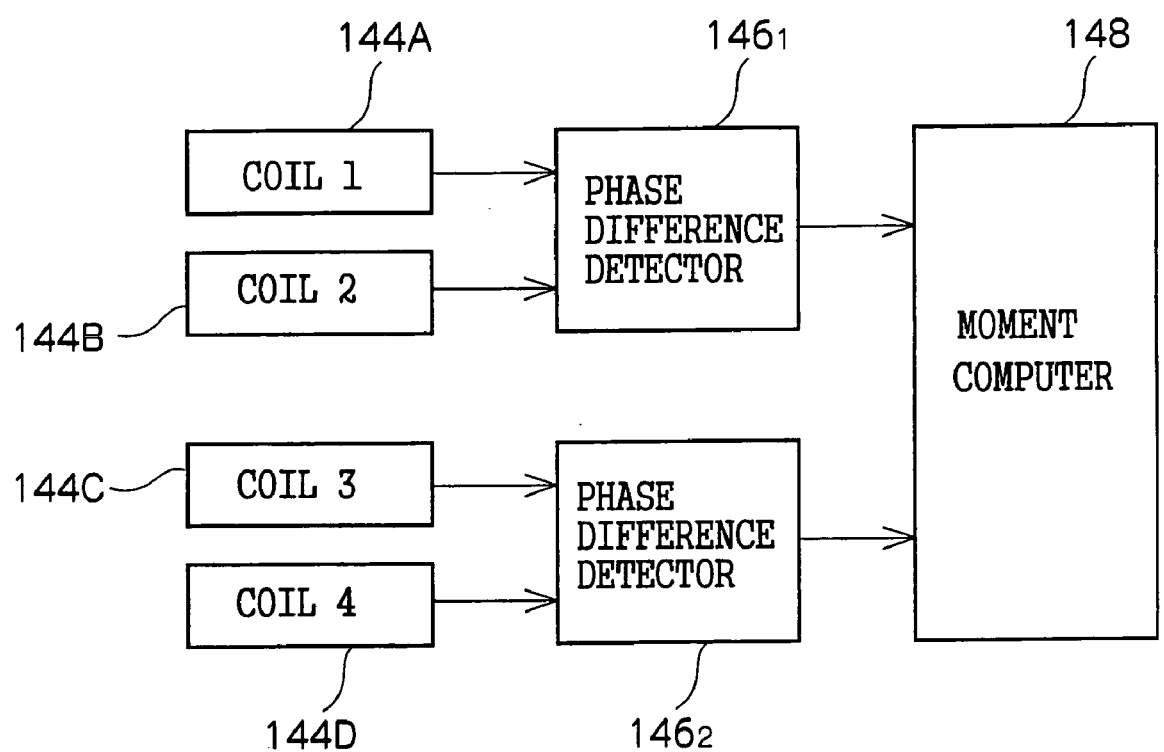
FIG. 34 is a block diagram showing the structure of a moment computing apparatus relating to the ninth embodiment.

As shown in FIG. 34, the moment detecting apparatus relating to the present embodiment is equipped with a phase difference detector $146_1$ connected to the coils 144A, 144B, a phase difference detector $146_2$ connected to the coils 144C, 144D, and the moment computer 148 connected to the phase difference detectors $146_1$, $146_2$.

Next, operation of the present embodiment will be described.

When the rotating element 102 rotates accompanying the permanent magnets 142, the induced voltages V1, V2 are generated at the two coils 144A, 144B respectively due to the electromagnetic induction with the permanent magnets 142, and the signals V1, V2 are outputted to the phase difference detector 1461. Further, induced voltages V3, V4 are generated at the two coils 144C, 144D respectively, and signals V3, V4 are outputted to the phase difference detector $146_2$.

As shown in FIG. 33, in a case in which the rotating element 102 rotates in the direction of the arrow, when the position of the rotating shaft is offset in the vertical direction, a phase difference $\psi_{V1V2}$ arises between the induced voltages V1, V2 of the coils 144A, 144B. Further, when the position of the rotating shaft is offset in the horizontal direction, a phase difference $\psi_{V3V4}$ arises between the induced voltages V3, V4 of the coils 144C, 144D. The phase difference detector $146_1$ detects the phase difference $\psi_{V1V2}$ from the inputted signals V1, V2, and outputs it to the moment computer 148. Further, the phase difference detector $146_2$ detects the phase difference $\psi_{V3V4}$ from the inputted signals V3, V4, and outputs it to the moment computer 148.

The relationship between the phase difference $\psi_{V1V2}$ and the moment Mx and the relationship between the phase difference $\psi_{V3V4}$ and the moment Mz are measured in advance and are stored in the moment computer 148 in a memory or the like by maps, data tables, relational expressions, or the like. In a case in which the phase difference $\psi_{V1V2}$ is detected, the moment computer 148 computes the moment Mx on the basis of the relationship which is stored in advance and the detected phase difference $\psi_{V1V2}$. In a case in which the phase difference $\psi_{V3V4}$ is detected, the moment computer 148 computes the moment Mz on the basis of the relationship which is stored in advance and the detected phase difference $\psi_{V3V4}$.

As described above, the conventional structure of merely determining the composite moment is divided in the present embodiment into the moment around an imaginary axis in the horizontal direction of the tire and the moment around an imaginary axis in the vertical direction, and each of the moments can be detected.

Note that, in the ninth embodiment, an example is described in which two coils are disposed on an imaginary axis in the tire horizontal direction, and two coils are disposed on an imaginary axis in the tire vertical direction. However, it suffices to be able to detect the phase difference, which is generated in accordance with the amount of offset of the rotating shaft, by an arbitrary combination of coils, and the number of coils and the arrangement thereof are not limited to those described above. For example, an inclined imaginary axis which intersects the tire vertical direction at a predetermined angle (e.g., 45°) can be arbitrarily set, and coils can be disposed on this imaginary axis.

What is claimed is:

1. A detecting apparatus comprising:
  a plurality of signal generating devices each generating a signal whose magnitude varies periodically in accordance with a positional change of a rotating shaft, which is a base for rotation of a rotating body and whose position is offset when force is applied thereto, and in accordance with a rotational state of the rotating body, the signal generating devices being disposed at predetermined positions such that phases of the generated signals are different;
  a characteristic amount detecting device detecting a characteristic amount corresponding to an amount of positional offset of the rotating shaft from a rotational axis of the rotating shaft, on the basis of the signals generated by the plurality of signal generating devices; and
  a moment detecting device detecting a moment applied to the rotating shaft on the basis of the characteristic amount detected by the detecting device, and on the basis of a relationship which is determined in advance on the basis of a shaft stiffness of the rotating shaft and the characteristic amount which varies in accordance with the positional offset of the rotating shaft.

2. The detecting apparatus of claim 1, further comprising a pulse generating device generating pulses, whose periods correspond to a rotational angle of the rotating body and the positional offset of the rotating shaft, from the signals generated by the plurality of signal generating devices,
  wherein the characteristic amount detecting device detects the characteristic amount from the pulses generated by the pulse generating device.

3. The detecting apparatus of claim 2, wherein the characteristic amount detecting device is structured by:
  a speed change rate computing device determining a speed change rate for each pulse of the rotating body accompanying a positional change of the rotating shaft, from the period of each pulse generated by the pulse generating device during one period of the rotating body, and an average value of a rotational speed of the rotating body during one period of the rotating body; and a higher-order component computing device detecting, as the characteristic amount, a predetermined higher-order component of the determined speed change rate of the rotating body.

4. The detecting apparatus of claim 1, wherein the signal generating devices generate the signals on the basis of variations in magnetic flux between a fixed element and a rotating element which rotates together with the rotating body.

5. The detecting apparatus of claim 1, wherein the characteristic amount detecting device detects, as the characteristic amount, an amount which is dependent on a phase difference of the signals generated by the plurality of signal generating devices.

6. The detecting apparatus of claim 5, wherein the characteristic amount detecting device detects, as the characteristic amount, an amount of offset of a signal generated by calculating a product of the signals generated by the plurality of signal generating devices.

7. The detecting apparatus of claim 1, wherein the characteristic amount detecting device detects, as the characteristic amount, an amount which is dependent on an amplitude of a signal generated by calculating a difference between the signals generated by the plurality of signal generating devices.

8. The detecting apparatus of claim 1, further comprising:
a rotational angle detecting device detecting a rotational angle of the rotating body; and
an amplitude detecting device determining amplitudes of the plurality of signals generated by the plurality of signal generating devices,
wherein, on the basis of the angle detected by the rotational angle detecting device, the characteristic amount detecting device detects, as the characteristic amounts, amplitudes of the plurality of signals determined by the amplitude detecting device when the rotational angle is a predetermined angle.

9. The detecting apparatus of claim 8, wherein the predetermined angle is an angle which is within a predetermined range which includes a rotational angle which is considered to be a rotational angle of the rotating body at which the amplitudes of the plurality of signals determined by the amplitude detecting device become maximums.

10. The detecting apparatus of claim 9, wherein the predetermined angle is the rotational angle which is considered to be the rotational angle of the rotating body at which the amplitudes of the plurality of signals become maximums, and is $(\pi/4)+n\cdot(\pi/2)$ where n is an integer of 0 or more.

11. The detecting apparatus of claim 1, wherein the shaft stiffness of the rotating shaft is a moment applied to the rotating shaft.

12. A detecting apparatus comprising:
a plurality of signal generating devices each generating a signal whose magnitude varies periodically in accordance with a positional change of a rotating shaft, which is a base for rotation of a tire mounted to a vehicle and whose position is offset when force is applied thereto, and in accordance with a rotational state of the tire, the signal generating devices being disposed at predetermined positions such that phases of the generated signals are different;

a characteristic amount detecting device detecting a characteristic amount corresponding to an amount of positional offset of the rotating shaft, on the basis of the signals generated by the plurality of signal generating devices; and a tire generated force detecting device detecting a tire generated force generated between the tire and a road surface, on the basis of information regarding mechanisms of the tire, and on the basis of the characteristic amount detected by the characteristic amount detecting device, and on the basis of a relationship which is determined in advance on the basis of a shaft stiffness of the rotating shaft and the characteristic amount which varies in accordance with the positional change of the rotating shaft.

13. A detecting apparatus comprising:
a plurality of signal generating devices each generating a signal whose magnitude varies periodically in accordance with a positional change of a rotating shaft, which is a base for rotation of a tire mounted to a vehicle and whose position is offset when force is applied thereto, and in accordance with a rotational state of the tire, the signal generating devices being disposed at predetermined positions such that phases of the generated signals are different;
a rotational angle detecting device detecting a rotational angle of the tire;
an amplitude detecting device determining amplitudes of the plurality of signals generated by the plurality of signal generating devices;
a detecting device detecting, on the basis of the angle detected by the rotational angle detecting device and the amplitudes of the plurality of signals detected by the amplitude detecting device, a difference between a rotational angle of the tire at which the amplitudes of the plurality of signals become maximums and a rotational angle which is considered to be a rotational angle of the tire at which the amplitudes of the plurality of signals become maximums, and the peaks of the amplitudes of the plurality of signals; and
a moment detecting device detecting a moment around an imaginary axis which exists within a plane which is perpendicular to the rotating shaft of the tire, on the basis of the difference in the rotational angles and the peaks which were detected by the detecting device.

14. A detecting apparatus comprising:
a pair of signal generating devices each generating a signal whose magnitude varies periodically in accordance with a positional change of a rotating shaft, which is a base for rotation of a tire mounted to a vehicle and whose position is offset when force is applied thereto, and in accordance with a rotational state of the tire, the signal generating devices being disposed at predetermined positions such that phases of the generated signals are different, and being disposed at positions which are offset from one another by a tire rotational angle of 180°, and being disposed at positions which are symmetrical with respect to an imaginary axis in a vertical direction of the tire;
a detecting device detecting a difference between the signals generated by the pair of signal generating devices; and
a moment detecting device detecting a moment around an imaginary axis which exists within a plane which is perpendicular to the rotating shaft of the tire, on the basis of the difference between the signals generated by the pair of signal generating devices which difference was detected by the detecting device.

15. A detecting apparatus comprising:
a pair of signal generating devices each generating a signal whose magnitude varies periodically in accordance with a positional change of a rotating shaft, which is a base for rotation of a tire mounted to a vehicle and whose position is offset when force is applied thereto, and in accordance with a rotational state of the tire, the signal generating devices being disposed on an imaginary axis in a tire vertical direction at positions which are offset from one another by a tire rotational angle of 180°;
a detecting device detecting a difference between the signals generated by the pair of signal generating devices; and
a moment detecting device detecting a moment around an imaginary axis in a horizontal direction of the tire, on the basis of the difference between the signals generated by the pair of signal generating devices which difference was detected by the detecting device.

16. A detecting apparatus comprising:
a plurality of signal generating devices each generating a signal whose magnitude varies periodically in accordance with a positional change of a rotating shaft, which is a base for rotation of a rotating body attached to a vehicle and whose position is offset when force is applied thereto, and in accordance with a rotational state of the rotating body, the signal generating devices being disposed at predetermined positions such that phases of the generated signals differ when a positional change of the rotating shaft arises;
a detecting device detecting a phase difference of the signals generated by the signal generating devices; and
a moment detecting device detecting a moment applied to the rotating shaft around an imaginary axis that is substantially perpendicular to a rotational axis of the rotating shaft, on the basis of the phase difference detected by the detecting device.

17. A detecting apparatus comprising:
a plurality of signal generating devices each generating a signal whose magnitude varies periodically in accordance with a positional change of a rotating shaft, which is a base for rotation of a tire mounted to a vehicle and whose position is offset when force is applied thereto, and in accordance with a rotational state of the tire, the signal generating devices being disposed at predetermined positions such that phases of the generated signals differ when a positional change of the rotating shaft arises;
a detecting device detecting a phase difference of the signals generated by the signal generating devices;
a moment detecting device detecting a moment around an imaginary axis which exists within a plane which is perpendicular to the rotating shaft of the tire, on the basis of the phase difference detected by the detecting device; and
a tire generated force detecting device detecting a tire generated force on the basis of the moment detected by the moment detecting device.

* * * * *